(12) United States Patent
Sagel et al.

(10) Patent No.: US 11,839,666 B2
(45) Date of Patent: *Dec. 12, 2023

(54) ORAL CARE ARTICLE COMPRISING A HYDROPHOBIC DELIVERY CARRIER AND SOLID HYDROPHILIC PARTICLES COMPRISING AN AGENT

(71) Applicant: The Procter & Gamble Company, Cincinnati, OH (US)

(72) Inventors: Paul Albert Sagel, Maineville, OH (US); Jayanth Rajaiah, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 85 days.

This patent is subject to a terminal disclaimer.

(21) Appl. No.: 17/481,397

(22) Filed: Sep. 22, 2021

(65) Prior Publication Data

US 2022/0117864 A1 Apr. 21, 2022

Related U.S. Application Data

(60) Provisional application No. 63/093,523, filed on Oct. 19, 2020, provisional application No. 63/093,518, filed on Oct. 19, 2020, provisional application No. 63/093,513, filed on Oct. 19, 2020, provisional application No. 63/093,536, filed on Oct. 19, 2020, provisional application No. 63/093,529, filed on Oct. 19, 2020.

(51) Int. Cl.
| A61K 8/02 | (2006.01) |
| A61K 8/22 | (2006.01) |
| A61K 8/81 | (2006.01) |
| A61Q 11/00 | (2006.01) |

(52) U.S. Cl.
CPC .......... *A61K 8/0204* (2013.01); *A61K 8/0208* (2013.01); *A61K 8/0233* (2013.01); *A61K 8/22* (2013.01); *A61K 8/8176* (2013.01); *A61Q 11/00* (2013.01); *A61K 2800/412* (2013.01); *A61K 2800/56* (2013.01); *A61K 2800/81* (2013.01); *A61K 2800/88* (2013.01)

(58) Field of Classification Search
CPC .............. A61K 7/20; A61K 8/89; A61K 8/81
USPC .......................................................... 424/53
IPC ...................................................... A61Q 11/00
See application file for complete search history.

(56) References Cited

U.S. PATENT DOCUMENTS

| 5,914,120 | A | * | 6/1999 | Wellinghoff | ........... | A01N 59/00 424/405 |
| 6,685,915 | B2 | | 2/2004 | Uzgiris et al. | | |
| 7,011,523 | B2 | | 3/2006 | Allred et al. | | |
| 8,376,746 | B2 | | 2/2013 | Brown et al. | | |
| 8,414,293 | B2 | | 4/2013 | Dillon et al. | | |
| 8,623,388 | B2 | | 1/2014 | Rajaiah | | |
| 8,986,005 | B2 | | 3/2015 | Montgomery | | |
| 9,320,692 | B2 | | 4/2016 | Tung | | |
| 9,682,256 | B2 | | 6/2017 | Boyd et al. | | |
| 10,780,032 | B1 | | 9/2020 | Rajaiah et al. | | |
| 2003/0003421 | A1 | | 1/2003 | Bestenheider | | |
| 2003/0235605 | A1 | * | 12/2003 | Lelah | ...................... | A01N 25/18 424/661 |
| 2005/0008584 | A1 | | 1/2005 | Montgomery | | |
| 2005/0063923 | A1 | * | 3/2005 | Prencipe | .............. | A61K 8/8176 424/53 |
| 2008/0274067 | A1 | | 11/2008 | Chaffer | | |
| 2009/0023106 | A1 | | 1/2009 | Jacobs | | |
| 2009/0238776 | A1 | * | 9/2009 | Baig | ...................... | A61Q 11/00 424/49 |
| 2016/0015496 | A1 | | 1/2016 | Johnson et al. | | |
| 2016/0230007 | A1 | | 8/2016 | Johnson et al. | | |
| 2019/0201296 | A1 | | 7/2019 | Wang et al. | | |
| 2020/0330784 | A1 | | 10/2020 | Sagel et al. | | |

FOREIGN PATENT DOCUMENTS

| EP | 3315118 A1 | 10/2016 |
| EP | 3984520 A1 | 4/2022 |
| EP | 3984521 A1 | 4/2022 |
| WO | 03015656 A2 | 2/2003 |
| WO | 200105629 A2 | 12/2004 |
| WO | 2005110344 A1 | 11/2005 |

(Continued)

OTHER PUBLICATIONS

All Office Actions for U.S. Appl. No. 17/481,377, filed Sep. 22, 2021.
All Office Actions for U.S. Appl. No. 17/481,498, filed Sep. 22, 2021.
All Office Actions for U.S. Appl. No. 17/481,509, filed Sep. 22, 2021.
All Office Actions for U.S. Appl. No. 17/481,524, filed Sep. 22, 2021.
Extended EP Search Report and Written Opinion for 20206902.7 dated May 3, 2021, 11 pages.

(Continued)

*Primary Examiner* — Walter E Webb
(74) *Attorney, Agent, or Firm* — Elizabeth A. Conklin

(57) ABSTRACT

An oral care article in form of a strip for use in the oral cavity. The oral care article comprises a solid hydrophobic delivery carrier comprising solid hydrophilic particles comprising an active agent for oral care. The active agent(s) for oral care can include bleaching agent(s), antimicrobial agent(s), anti-calculus agent(s), healing agent(s), anti-caries agent(s), dentinal desensitizing agent(s), anesthetic agent(s), antifungal agent(s), coolant(s), anti-inflammatory agent(s), selective H-2 antagonist(s), nutrient(s), erythritol, probiotics, fluoride ion source(s), or combinations thereof. The concentration of the active agent for oral care at a first surface of the solid hydrophobic delivery carrier is greater than the concentration of the active agent at a second surface of the solid hydrophobic delivery carrier.

26 Claims, 4 Drawing Sheets

(56) References Cited

FOREIGN PATENT DOCUMENTS

WO     2013096321 A2     6/2013
WO     2018080987 A1     5/2018

OTHER PUBLICATIONS

Extended EP Search Report and Written Opinion for 21198154.3 dated Feb. 22, 2022, 12 pages.
PCT Search Report and Written Opinion for PCT/US2021/051393 dated Dec. 10, 2021, 17 pages.

* cited by examiner

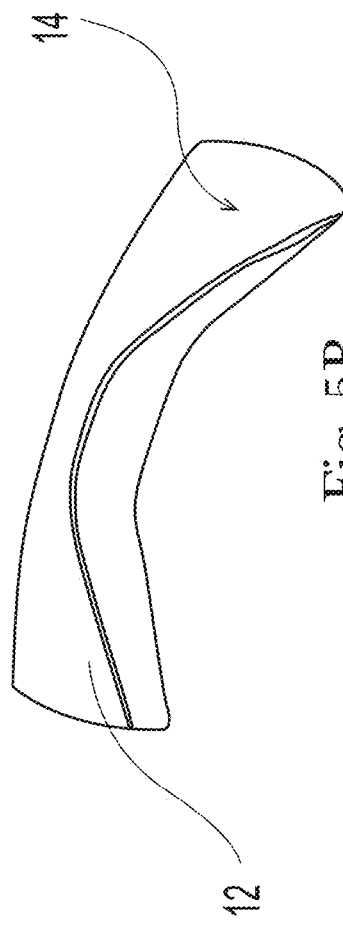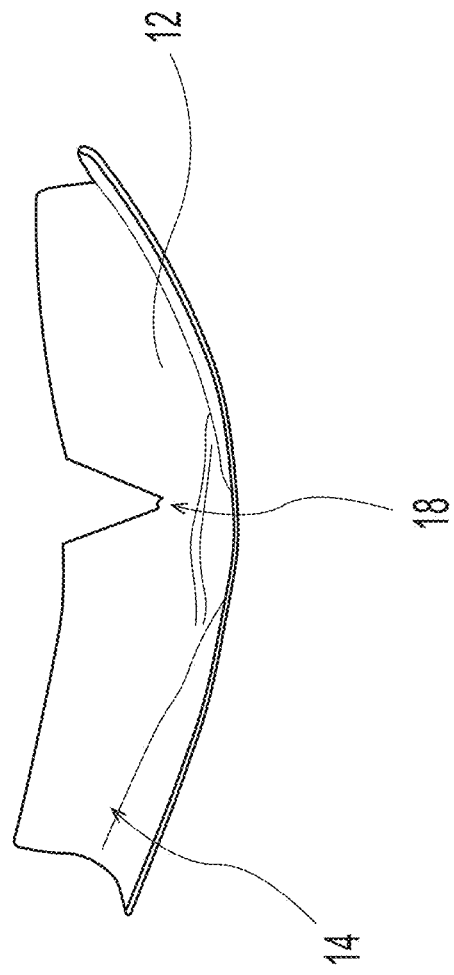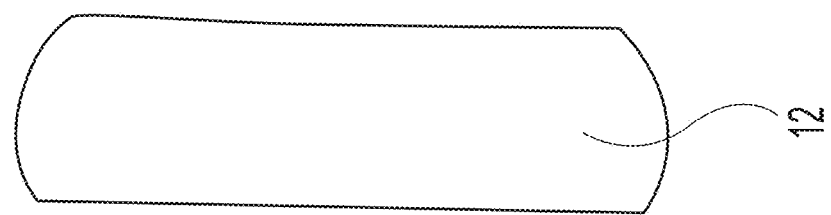

ORAL CARE ARTICLE COMPRISING A HYDROPHOBIC DELIVERY CARRIER AND SOLID HYDROPHILIC PARTICLES COMPRISING AN AGENT

FIELD OF THE INVENTION

The present invention relates to oral care articles comprising a hydrophobic delivery carrier and solid hydrophilic particles comprising an active agent for oral care suitable for use in the oral cavity.

BACKGROUND OF THE INVENTION

Currently in the marketplace are dental products by which various cosmetic and/or therapeutic actives are delivered to teeth and the oral cavity. Examples of such products include brushing aids, such as dentifrice products for delivery of oral care actives for example polyphosphates or fluorides; mouthwashes containing breath fresheners or antibacterial actives; and whitening strips for the delivery of bleaching actives to the teeth. The use of a dental strip has been recognized as a convenient and inexpensive way to deliver cosmetic and therapeutic benefits to the teeth and mucosal surfaces of the oral cavity; for example, dental whitening strips, where a whitening composition is applied to a strip and thereafter applied to the teeth to achieve sustained contact between the teeth and the whitening article.

Despite the above known approaches for the treatment or improvement of oral conditions, especially for the whitening of teeth or the application of fluoride, a need still exists for providing products with improved performance, e.g. increased speed of whitening, improved bleaching efficacy, higher anti-bacterial effects, higher fluoride retention, decreased tooth-sensitivity, and/or decreased oral soft tissue irritation. Previous attempts to address these issues include increasing the level of the active agent in the articles. This approach, however, can present problems. The user may experience increased irritation and/or sensitivity which may be associated with using an increased amount of an active agent. Therefore, despite the above known approaches for the treatment or improvement of oral conditions, especially for the whitening of teeth, a need still exists for providing products with improved bleaching efficacy, increased speed of whitening, decreased tooth-sensitivity, and/or decreased oral soft tissue irritation.

SUMMARY OF THE INVENTION

The present invention relates to an oral care article comprising:
a) a solid hydrophobic delivery carrier in form of a strip having a length and a width forming a first surface and having a thickness extending from the first surface to a second surface, wherein the solid hydrophobic delivery carrier has an average thickness of less than about 3 mm; and
b) solid hydrophilic particles comprising an active agent for oral care comprising at least one of healing agent(s), anti-calculus agent(s), anti-caries agent(s), antimicrobial agent(s), dentinal desensitizing agent(s), anesthetic agent(s), antifungal agent(s), coolant(s), anti-inflammatory agent(s), selective H-2 antagonist(s), nutrient(s), erythritol, probiotics, fluoride ion source(s), hydrophilic bleaching agent(s), tooth whitening agent(s), or combinations thereof;
wherein the solid hydrophilic particles are disposed in and embedded in the solid hydrophobic delivery carrier, wherein the solid hydrophilic particles are disposed i) at least partially below the first surface, and ii) at least partially at or above the first surface of the solid hydrophobic delivery carrier; and
wherein the concentration of the active agent at the first surface is greater than the concentration of the active agent at the second surface.

The present article may be used to deliver health, therapeutic or cosmetic benefits to the oral cavity by directly applying the oral care active agent to the teeth and/or the oral cavity. In one embodiment, the article of the present invention can be used for reducing and/or removing caries, plaque, and tartar, promoting gum health, preventing and treating cavities, improving breath, providing antibacterial effects and/or a combination thereof.

The present article may be used to deliver cosmetic and/or non-therapeutic benefits to the oral cavity by directly applying the oral care active agent to the teeth and/or the oral cavity. In one embodiment, the article of the present invention can be used for reducing and/or removing stain, promoting bleaching, and/or a combination thereof.

The article may be provided as a kit, for example together with an apparatus for increasing the efficacy of the oral care active agent(s), such as an electromagnetic radiation source.

The article may be further provided together with instructions to use the article.

The article is directly attached to the teeth or the oral cavity, i.e. the adhesion function or attachment mechanism can be provided directly by the article, e.g. the hydrophobic delivery carrier itself. For example, the article may optionally be of sufficient size that once applied the article overlaps with the oral soft tissues rendering more of the teeth surface available for the effect achieved with the oral care active agent(s). The article may be attached to the oral cavity by physical interference or mechanical inter-locking between the article and the oral surfaces including the teeth.

There is further disclosed a process for making an oral care article, the process comprising the steps of: (i) providing a solid hydrophobic delivery carrier in the form of a strip having a length and a width forming a first surface and having a thickness extending from the first surface to a second surface, wherein the average thickness may be less than about 3 mm; (ii) applying solid hydrophilic particles comprising a bleaching agent to the first surface of the solid hydrophobic delivery carrier, wherein the level of bleaching agent may be of from about 0.01% to about 15%, by total weight of the solid hydrophobic delivery carrier and solid hydrophilic particles; and (iii) forcing the solid hydrophilic particles into the first surface of the solid hydrophobic delivery carrier, thereby embedding the solid hydrophilic particles into the solid hydrophobic delivery carrier.

BRIEF DESCRIPTION OF THE DRAWINGS

FIG. 5A is a photograph image of an article 10 in strip form formed into a dental tray (FIG. 5B) comprising a notch 18 (FIG. 5C);

FIG. 8A is an image of a first surface 14, and FIG. 8B is an image of a second surface 16.

DETAILED DESCRIPTION OF THE INVENTION

Figure 1:
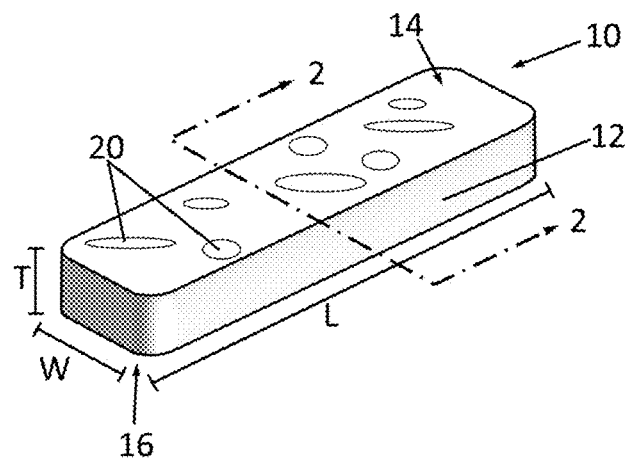
FIG. 1 is a perspective view of an article 10 in strip form having rounded corners comprising solid hydrophilic particles 20.

It has surprisingly been found that oral care active agent(s) can be effective at very low concentrations, by weight of an oral care article, if they are provided as solid hydrophilic particles and combined with a hydrophobic delivery carrier to form an oral care article as disclosed herein. The oral care article of the present invention can comprise, from about 0.01% to about 50% or from about 0.1% to about 30%, or from about 0.2% to about 25%, or from about 0.1% to about 15%, or from about 0.3% to about 10%, by weight of the article, of solid hydrophilic particles comprising an oral care active agent; wherein the solid hydrophilic particles are soluble in water, swell upon contact with water, and/or release the oral care active agent upon contact with water or water comprising liquids.

The solid hydrophilic particles are disposed on and in by being embedded in, the hydrophobic delivery carrier to form the oral care article of the present invention. The solid hydrophilic particles comprise the at least one oral care active agent(s), wherein the concentration of the oral care active agent at a first surface of the hydrophobic delivery carrier is greater than the concentration of the oral care active agent at a second surface. Examples for the at least one oral care active agent(s) comprise healing agent(s), anti-calculus agent(s), anti-caries agent(s), antimicrobial agent(s), dentinal desensitizing agent(s), anesthetic agent(s), antifungal agent(s), coolant(s), anti-inflammatory agent(s), selective H-2 antagonist(s), nutrient(s), erythritol, probiotics, fluoride ion source(s), hydrophilic bleaching agent(s), tooth whitening agent(s), or combinations thereof, wherein bleaching agent(s), antimicrobial agent(s), and/or anticaries agent(s) are preferred. Without wishing to be bound by theory, it is believed that when the article contacts the surface of a tooth with the first surface, the solid hydrophilic particles that are embedded in the hydrophobic delivery carrier deliver the actives to the hydrophilic biofilm on the surface of the tooth. This can lead to increased active efficacy such as tooth-whitening, anti-bacterial and/or anti-caries effects with lower total levels of oral care active agents.

The term "delivery carrier" as used herein comprises a material in the form of a strip that is used to deliver actives from solid hydrophilic particles to a surface, for example a tooth surface. A delivery carrier as used herein may be flat or pre-formed in a three-dimensional shape, for example in the shape of a dental arch. The material of the "delivery carrier" should be compatible with the oral cavity and comfortable for the user and is hydrophobic. Example materials for a hydrophobic delivery carrier include wax(es), polymer(s) and combinations thereof.

The terms "hydrophobic and "hydrophilic" are used herein according to common general knowledge. The term "hydrophilic" is used for object(s), article(s), molecule(s), compound(s), entity(s) that are attracted to water and other polar materials. The term "hydrophobic" is used accordingly for object(s), article(s), molecule(s), compound(s), entity(s) that are not attracted to and/or repelled by water and other polar materials The term "strip" as used herein comprises a material 1) whose longest dimension length is generally greater than its width, and 2) whose width is generally greater than its thickness. Strips may be rectangular, arched, curved, semicircular, have rounded corners to avoid irritation of the soft tissue of the oral cavity. "Rounded corners," as used herein means generally lacking sharp angles or points, for example one or more angles of 135° or less. In addition, a strip may be bent or shaped into three dimensional shapes, for example into a dental arch, or combinations thereof. Strips may be solid, textured, rigid, moldable, deformable, permanently deformable, or combinations thereof. Strips useful in the present invention may be suitably shaped to fit into an oral cavity.

The term "oral care article" as used herein refers to an article of manufacture for use in the oral cavity, for example for use on teeth in the oral cavity. The oral care article may comprise a solid hydrophobic delivery carrier combined with solid hydrophilic particles comprising at least one oral care active agent.

The term "unit-dose article" as used herein means an article that is used once and disposed of subsequently.

The term "removable article" as used herein means an article that is removed from the oral cavity after use.

The term "stick type product" as used herein refers to an article which is a bar of an apparently firm solid material held within a dispensing container which when applied to a surface to be treated, retains its structural integrity and shape. When a portion of the stick is drawn across a surface, a film of the stick article is transferred to the surface. Examples include lip balm and lipstick. A stick type product is generally used several times and thus, cannot be considered as a unit-dose article as used herein. In addition, when a portion of the stick type product is drawn across a surface a film of the stick composition is transferred to the surface which is generally not removed and/or removable from the oral cavity after use.

The term "moldable" as used herein means that the material the hydrophobic delivery carrier and/or the article conforms to the general shape of a dental arch when applied by the user. Examples of hydrophobic delivery carriers that are "moldable" include a casting wax clear sheet 24 gauge (reference number 114009 supplied by Freeman Manufacturing Company, Ohio, USA) cut into a strip about 0.51 mm thick, about 22 mm wide and about 62 mm long.

The term "wax" as used herein means organic compounds that are hydrophobic and solid at room temperature, for example higher alkanes. Waxes can have a drop melting point as measured by ASTM method D127-08 from about 60° C. to about 120° C., or from about 70° C. to about 110° C., or from about 80° C. to about 100° C., or from about 90° C. to about 100° C., and/or a needle penetration consistency value as measured by ASTM method D1321-16a from about 0.1 to about 100, or from about 0.5 to about 50, or from about 1 to about 10, and/or a cone penetration consistency value as measured by ASTM method D937-07 less than 10, or from about 1 to 10, or less than about 5.

The term "needle penetration consistency value" as used herein means the depth, in tenths of a millimeter, that a standard needle will penetrate the sample under fixed conditions of mass, time, and temperature. The needle penetration consistency value is measured according to ASTM method D1321-16a.

The term "cone penetration consistency value" as used herein means the depth, in tenths of a millimeter, that a standard cone will penetrate the sample under fixed conditions of mass, time, and temperature. The cone penetration consistency value is measured according to ASTM method D937-07.

The term "particle" as used herein is a discrete, solid material. Solid particles have dimensions larger than individual atoms or molecules and are typically sub-micron to about five millimeters in their largest dimension. Particles may be agglomerated into an agglomerate of discrete particles.

The term "solid hydrophilic particle" as used herein is a solid particle that is soluble in water and/or swells (increases in volume and/or weight) upon contact with water, and releases oral care active agent upon contact with water. In addition, the solid hydrophilic particle is insoluble in the hydrophobic delivery carrier. The solid hydrophilic particle comprises an oral care active agent which is released from the solid hydrophilic particle upon contact with water. For example, the solid hydrophilic particles may comprise bleaching agent(s), antimicrobial agent(s) and/or anticaries agent(s) as active agent(s). If an active agent is released, the active agent may be a gas, liquid, or solid dissolved in a liquid. The solid hydrophilic particles may further comprise ingredients that are water soluble, water miscible, or combinations thereof, such as for example: water, water-soluble solvents, alcohols, carbopol, polyalkylene glycols, humectants, glycerin, sorbitol, xylitol, butylene glycol, polyethylene glycol, and propylene glycol, and mixtures thereof. If these ingredients are added to or are present in the solid hydrophilic particles, the percentage of the solid hydrophilic particles in the article is calculated by excluding these ingredients. If water-insoluble or water-immiscible fillers are added to the solid hydrophilic particles, the percentage of the solid hydrophilic particles in the article is calculated by excluding these fillers.

The term "immiscible" or "insoluble" as used herein means less than 1 part by weight of the substance dissolves in 100 parts by weight of a second substance.

The term "solubility" as used herein is the maximum number of parts by weight of the substance that can dissolve in 100 parts by weight of a second substance.

The term "embedded" or "embedded particle" as used herein means that said solid particle is disposed i) at least partially below a surface, and ii) at least partially at or above the said surface of a solid hydrophobic delivery carrier. Examples of embedded particles include solid hydrophilic particles pressed into a surface of a wax sheet, e.g. a casting wax clear sheet 24 gauge (reference number 114009 supplied by Freeman Manufacturing Company, Ohio, USA) at for example 625 PSI (43,9418 kg/cm2) for 60 seconds.

The term "active agent" as used herein is a component present in the solid hydrophilic particle that provides a benefit for oral care. For example, the active agent may comprise bleaching agent(s), antimicrobial agent(s) and/or anticaries agent(s).

The term "bleaching agent" as used herein is an active agent that provides a bleaching or whitening benefit. For example, if urea peroxide (also known as urea hydrogen peroxide adduct) is used as a solid hydrophilic particle, the hydrogen peroxide component of the urea peroxide is a bleaching agent. Similarly, if a complex of hydrogen peroxide and polyvinylpyrrolidone (PVP) polymer is used as a solid hydrophilic particle, the hydrogen peroxide component of the complex of hydrogen peroxide and polyvinylpyrrolidone (PVP) polymer is a bleaching agent.

By "safe and effective amount" as used herein means an amount of a component, high enough to significantly (positively) modify the condition to be treated or to affect the desired results, but low enough to avoid serious side effects (at a reasonable benefit/risk ratio), within the scope of sound medical/dental judgment. The safe and effective amount of a component, will vary with the specific condition being treated, the age and physical condition of the patient being treated, the severity of the condition, the duration of treatment, the nature of concurrent therapy, the specific form employed, and the specific vehicle from which the component is applied.

By "a sufficient period of time to achieve the desired effect of the active" as used herein is meant that the article comprising the active may be used or worn by the participant or the participant may be instructed to use or wear the article comprising the active from about 10 seconds to about 24 hours, in one aspect from about 1 minute to about 2 hours, or from about 5 minutes to about 1 hour per application. The treatments may be applied from about 1 time a day to about 10 times a day, or from about 1 time a day to about 5 times a day, or from about 1 time a day to about 3 times a day. The treatments may be applied for from about 1 day to about 8 weeks, or from about 1 day to about 4 weeks, or from about 1 day to about 1 week. Further, the length of treatment to achieve the desired benefit, for example, tooth bleaching, may last for a specified period of time, which may be repeated if necessary, for example from about one day to about six months or ongoing. The optimal duration and frequency of application will depend on the desired effect, the severity of any condition being treated, the health and age of the user and like considerations.

The term "equivalent diameter" of a particle as used herein means the diameter of a sphere having the same volume as the particle.

All percentages and ratios used herein are by weight of the article (wt %), unless otherwise indicated. All percentages, ratios, and levels of ingredients referred to herein are based on the actual amount of the ingredient, and do not comprise solvents, fillers, or other materials with which the ingredient may be combined as a commercially available product, unless otherwise indicated.

All measurements referred to herein are made at about 23° C. (i.e. room temperature) unless otherwise specified.

"Active and other ingredients" useful herein may be categorized or described herein by their cosmetic and/or therapeutic benefit or their postulated mode of action or function. However, it is to be understood that the active and other ingredients useful herein can, in some instances, provide more than one cosmetic and/or therapeutic benefit or function or operate via more than one mode of action. Therefore, classifications herein are made for the sake of convenience and are not intended to limit an ingredient to the specifically stated function(s) or activities listed.

The term "orally acceptable" comprises one or more compatible solid or liquid excipients or diluents which are suitable for use in the oral cavity. By "compatible," as used herein, is meant that the components are capable of being commingled without interaction in a manner which would substantially reduce the article's stability and/or efficacy.

Oral Care Articles

The oral care articles as disclosed herein comprise a solid hydrophobic delivery carrier combined with solid hydrophilic particles comprising at least one oral care active agent embedded in the hydrophobic delivery carrier, wherein the concentration of said active agent at a first surface of the hydrophobic delivery carrier or article is greater than the concentration of the active agent at a second surface of the hydrophobic delivery carrier or article. The oral care active agent may be for example a bleaching agent, an antibacterial or an anticaries agent. The components and properties of the solid hydrophilic particles as well as of the hydrophobic delivery carrier are chosen to allow for an optimal release of the active agent readily from the article.

The articles as disclosed herein comprise a solid hydrophobic or solid water-insoluble delivery carrier with embedded solid hydrophilic particles comprising at least one oral care active agent, wherein the concentration of the active agent at a first surface of the hydrophobic delivery carrier is greater than the concentration of the active agent at a second surface of the hydrophobic delivery carrier.

The articles as disclosed herein may comprise a solid thermoplastic hydrophobic delivery carrier with embedded solid hydrophilic particles comprising at least one oral care active agent, wherein the concentration of the active agent at a first surface of the hydrophobic delivery carrier is greater than the concentration of the active agent at a second surface of the hydrophobic delivery carrier. Without wishing to be bound by theory it is believed that when the present article is brought into contact with a tooth surface, the solid hydrophilic particles deliver the active agent to the hydrophilic biofilm of the surface. The possible net effect is that the teeth treating effect is started only after contact with the tooth surface to be treated. That means, the hydrophilic active agent may be protected against environmental influence and thereby stabilized by the hydrophobic delivery carrier of the article until use as well as during use. Thereby, the active effect may be applied to the tooth surface and the hydrophilic active agent, e.g. a bleaching agent, anti-bacterial or anti-caries agent may be potentially shielded against the oral environment during use. Thereby the efficacy of the active agent may be enhanced and/or accelerated.

Without wishing to be bound by theory, the present invention may improve the delivery of the hydrophilic active agent to an oral cavity surface, such as a tooth or a gum surface, due to the partial hydrophobic and partial hydrophilic nature of the article. Due to the driving force resulting therefrom, the active agent may be driven towards the tooth surface. Thereby increased speed and/or increased efficacy of the active agent may be achieved, even though surprisingly low total levels of the active agent are used. The present invention, therefore, at a given total overall concentration, such as less than about 15%, less than about 10%, less than about 5%, less than about 3%, less than about 1%, less than about 0.1%, or below, by weight of an oral care active agent, may deliver a surprisingly high level of treatment efficacy, and thus may require fewer applications to get the same degree of efficacy compared to application of the prior art, or may require a lower concentration to get the same degree of efficacy. Without wishing to be bound by theory, it is believed that part of the reason for the high efficacy delivered by the articles of the present invention may be because they may be attached to the oral cavity by physical interference or mechanical inter-locking between the hydrophobic delivery carrier and the oral surfaces including the teeth, or are self-adhesive or self-substantive to teeth, and resistant to being washed away in saliva or other liquids. This may keep the active agents such as bleaching agents, antibacterial or anticaries agents in contact with the oral surface such as the tooth surface or in the oral cavity for a long time, thus leading to high efficacy. It is worth noting that in general substances that are adhesive or substantive to the oral cavity are hydrophilic because surfaces in the oral cavity are wet. It is also worth noting that some product forms, especially stick type products, may need an added substantivity agent to adhere the article to surfaces in the oral cavity. However, it has been found that the article of the present invention and/or the hydrophobic delivery carrier of the present invention may be attached to the oral cavity by physical interference or mechanical inter-locking between the hydrophobic delivery carrier and the oral surfaces including the teeth, or are self-adhesive or self-substantive to surfaces in the oral cavity such as tooth surfaces even without an added adhesive (for example hydrophilic particles that become sticky when activated by moisture, or hydrophilic liquids) or added substantivity agent. Achieving adhesiveness or substantivity without the use of an added hydrophilic adhesive or hydrophilic substantivity agent is especially useful because it may help make the article resistant to being washed away in saliva or other liquids—thus leading to higher efficacy. This is because achieving adhesiveness or substantivity without the use of an added hydrophilic adhesive or added hydrophilic substantivity agent can allow us to increase the level of hydrophobic components (that resist being washed away) and/or decrease the level of hydrophilic components (that are susceptible to being washed away). Counterintuitively, this can help increase the substantivity of the article leading to a high concentration of the oral care active agent or bleaching agent in contact with the oral surface such as the tooth surface or in the oral cavity for a long time, this in turn leading to high efficacy. Thus, the articles of the present invention and/or the hydrophobic delivery carrier of the present invention may be substantially free of an added adhesive, substantially free of an added hydrophilic adhesive (for example hydrophilic particles that become sticky when activated by moisture) or an added hydrophilic substantivity agent, and in one embodiment substantially free of an added hydrophilic liquid adhesive (for example glycerin). The article of the present invention and/or the hydrophobic delivery carrier of the present invention may be attached to the oral cavity by physical interference or mechanical inter-locking between the hydrophobic delivery carrier and the oral surfaces including the teeth, or are self-adhesive or self-substantive to the oral cavity such as the tooth surface.

It is also worth noting that some product forms, especially stick type products, may need an added active releasing agent or added peroxide releasing agent to improve the release of the active or peroxide trapped in the stick type product. In general, active releasing agents or peroxide releasing agents are hydrophilic water-soluble or water-swellable polymers or hydrophilic liquids that may provide hydration channels in the article allowing water to penetrate the article and allowing the active or peroxide to leach out. An added peroxide releasing agent (such as sodium percarbonate) may help break the hydrophobic matrix as a result of micro bubbles that may be generated when it comes in contact with water; and this disruption may enhance the release of the whitening or oral care active agents, such as the hydrogen peroxide. However, the articles of the present invention may be self-releasing (for example, they release active or peroxide even without an added active releasing agent or an added peroxide releasing agent).

The retention of the article on the tooth surfaces may be improved as the hydrophobic delivery carrier resists salivary dilution and salivary enzymes which can decompose the active, such as peroxide. Even furthermore, the hydrophobic delivery carrier does not dehydrate the teeth creating an outward flux of water created by many hydrophilic articles containing hydrophilic adhesives such as polycarboxylic acid. Since the hydrophobic delivery carrier does not dehydrate the teeth it may result in a surprisingly low level of tooth sensitivity even while delivering a surprisingly high level of active efficacy, such as bleaching efficacy.

The hydrophobic delivery carrier may provide further advantages. For example, the hydrophobic delivery carrier may represent a stable matrix for ingredients which are soluble in the hydrophobic delivery carrier. For example, many flavor ingredients usually used in oral care articles are soluble in the hydrophobic delivery carrier. That means the flavor ingredients may be protected from any influence of the hydrophilic oral care active agent, for example a bleaching agent, in the oral care article. During use of the article at the tooth surface at least part of the hydrophobic delivery carrier may be located towards the soft oral tissues, such as the mucosa, thereby presenting the ingredients which are present in the hydrophobic delivery carrier, such as flavor compounds, to the oral cavity. For example, flavor ingredients may be located at the second surface of the hydrophobic delivery carrier so that the solid hydrophilic particles and an optional flavor ingredient are located at opposite sides of the hydrophobic delivery carrier and can be released independently to the oral cavity. The hydrophobic delivery carrier may shield the oral care active agent, such as a bleaching agent against any influence from the oral cavity, such as dilution by saliva. The shielding effect may also apply to the tooth surface(s) themselves, wherein the hydrophobic delivery carrier may provide greater hydration of the teeth surfaces.

It is worth noting that stick type products may be unhygienic for repeated use inside the oral cavity due to potential contamination or bio-film build-up. Saliva or moisture may penetrate the stick type product when used inside the oral cavity and this may degrade the active agents especially bleaching agents such as peroxides during storage between uses; and this degradation may be further accelerated by enzymes present in saliva. Furthermore, this degradation could be most pronounced at the tip of the stick type product that comes in direct contact with the saliva or moisture inside the oral cavity, leading to diminished efficacy the next time the stick type product is used. This "contact-degrade-contact" cycle may be repeated every time the stick type product is used—leading to most if not all applications after the first application being less efficacious.

It is worth noting that articles of the present invention may be provided in a unit-dose form that is used once and disposed of subsequently. This unit-dose form can provide several advantages over other product forms including stick type products, such as: 1) a high level of hygienic protection since it is used once and disposed of, 2) since the unit-dose form provides a pre-measured dose of the active agent, e.g. bleaching agent, in every dose, it takes the guesswork out of estimating how much product to use (which can be confusing or even intimidating to consumers who are not familiar with the product), and 3) since the solid hydrophilic particles can be distributed across the article, it can minimize spots that are over-treated or under-treated, and 4) since the active agent, e.g. bleaching agent, is not exposed to the environment or the oral cavity until the time of use, the potency of the active agent, e.g. bleaching agent, may be maintained for longer periods of time.

In another aspect, articles of the present invention may be removed from the oral cavity after use. This, in contrast to stick type products, allows the user to remove and discard any active agent, e.g. bleaching agent leftover after the treatment period has been completed. The article of the present invention may be a single layer.

Hydrophobic Delivery Carrier

The article(s) as disclosed herein comprise a solid hydrophobic delivery carrier combined with solid hydrophilic particles comprising at least one oral care active agent embedded in the hydrophobic delivery carrier. The hydrophobic delivery carrier or article may be attached to the oral cavity by physical interference or mechanical inter-locking between the hydrophobic delivery carrier and the oral surfaces including the teeth. For example, the hydrophobic delivery carrier or article may be of sufficient size that, once applied the hydrophobic delivery carrier overlaps with the oral soft tissues rendering more of the teeth surface available for the treatment. The basic form of the hydrophobic delivery carrier or article is a strip having a length and a width forming a first and a second surface separated by a thickness from each other. In addition, the basic form of the hydrophobic delivery carrier or article may also be formed into any shape or size suitable to contact the desired oral surface, for example into the form of a dental arch.

The form of said first surface may be substantially flat, may have irregularities due to embedded solid hydrophilic particles, may be shaped into three dimensional shapes for example in the shape of a dental arch or teeth, or combinations thereof. In general, the first surface and the second surface of the hydrophobic delivery carrier or article are similar in size and shape, adjacent to each other or nested, and separated by an average distance of no more than about 3 mm. For example, the average distance between the first surface and the second surface of the hydrophobic delivery carrier or article may be from about 0.01 mm to about 3 mm, or from about 0.1 mm to about 2 mm, or from about 0.15 mm to about 1 mm, or from about 0.25 mm to about 0.75 mm. The article of the present invention may be a single layer.

The basic form of the hydrophobic delivery carrier or article is a strip having a length, a width, and a thickness. The average length of the hydrophobic delivery carrier or article may be in the range from about 35 mm to about 100 mm, or from about 40 mm to about 90 mm, or from about 50 mm to about 80 mm. The average width of the hydrophobic delivery carrier or article may be in the range from about 3 mm to about 30 mm, or from about 5 mm to about 25 mm, or from about 15 mm to about 25 mm.

Without wishing to be bound by theory the average thickness of the hydrophobic delivery carrier or article may be a factor to ensure that the article: 1) is comfortable during use, and/or 2) releases an effective amount of the active agent per cm2 during use. Specifically, for a given % active agent, if the average thickness of the hydrophobic delivery carrier or article is too low, the active agent may be spread across a large area of a first surface and consequently deliver a low level of active agent per cm2 leading to decreased efficacy. In contrast, if the average thickness of the hydrophobic delivery carrier or article is too high, the article may be too bulky and not comfortable during use. The average thickness of the hydrophobic delivery carrier or article may be in the range 0.01 mm to about 3 mm, or from about 0.1 mm to about 2 mm, or from about 0.15 mm to about 1 mm, or from about 0.25 mm to about 0.75 mm.

The hydrophobic delivery carrier may be transparent or translucent to electromagnetic radiation with wavelengths from about 200 nm to about 1700 nm.

Without wishing to be bound by theory the drop melting point of the hydrophobic delivery carrier may be a factor to ensure that the article: 1) does not melt or become sticky during storage, and/or 2) releases an effective amount of the active agent during use. Specifically, if the drop melting point of the hydrophobic delivery carrier is too low, the article may melt or become sticky during storage. In contrast, if the drop melting point of the hydrophobic delivery carrier is too high, the article may not release an effective amount of the active agent during use. For example, the drop melting point of a suitable hydrophobic delivery carrier may be in the range of from about 60° C. to about 120° C., or from about 70° to about 110° C., or from about 80° C. to about 100° C., or from about 90° C. to about 100° C.

Without wishing to be bound by theory, the needle penetration consistency value of the hydrophobic delivery carrier may be a factor to ensure that the article: 1) does not become sticky during storage, and/or 2) releases an effective amount of the active agent during use. Specifically, if the needle penetration consistency value of the hydrophobic delivery carrier is too high, the article may become sticky during storage. In contrast, if the needle penetration consistency value of the hydrophobic delivery carrier is too low, the article may not release an effective amount of the active agent during use. The needle penetration consistency value of the hydrophobic delivery carrier may be in the range of from about 0.1 to about 100, or from about 0.5 to about 50, or from about 1 to about 10.

Without wishing to be bound by theory, the cone penetration consistency value of the hydrophobic delivery carrier may be a factor to ensure that the article: 1) does not become sticky during storage, and/or 2) releases an effective amount of the active agent during use. Specifically, if the cone penetration consistency value of the hydrophobic delivery carrier is too high, the article may become sticky during storage. In contrast, if the cone penetration consistency value of the hydrophobic delivery carrier is too low, the article may not release an effective amount of the active agent during use. The cone penetration consistency value of the hydrophobic delivery carrier may be less than about 10, or from about 1 to about 9, or less than about 5.

The hydrophobic delivery carrier or article of the present invention may be moldable. Being moldable may allow the hydrophobic delivery carrier to be shaped into the form of a dental arch or to the surface contour of the teeth. An optimal adaptation to the tooth surface allows 1) an effective release of the active agent and/or 2) a comfortable experience during use. In one aspect the permanent deformation occurs under minimum normal force being applied by the wearer, in one aspect the hydrophobic delivery carrier or article substantially conforms to a shape of a tooth via permanent deformation under a pressure less than about 250,000 Pascals.

The hydrophobic delivery carrier of the present invention may be rigid. The rigidity of the hydrophobic delivery carrier or article may be a factor to ensure that 1) it is easy to handle and position accurately during application, and/or 2) it keeps the given shape during use. Flexural stiffness is a material property that is a function of a combination of strip of material thickness, width and material modulus of elasticity. The test described below is a method for measuring the rigidity of strips and sheeting. It determines the resistance to flexure of a sample by using a strain gauge affixed to the end of a horizontal beam. The opposite end of the beam presses across a strip of the sample to force a portion of the strip into a vertical groove in a horizontal platform upon which the sample rests. A microammeter wired to the strain gauge is calibrated in terms of deflection force. The rigidity of the sample is read directly from the microammeter and expressed as grams per centimeter of the sample strip width. Specifically, if the flexural stiffness of the hydrophobic delivery carrier or article is too high, it may not be moldable and may break during shaping at the tooth surface. In contrast, if the flexural stiffness of the hydrophobic delivery carrier or article is too low, it may not be easy to handle and position accurately during application. For example, the flexural stiffness of the hydrophobic delivery carrier may be greater than 50 g/cm, or from about 75 g/cm to about 1000 g/cm, or from about 200 g/cm to about 500 g/cm as measured by ASTM D2923-95.

The delivery carrier of the present invention is hydrophobic. The hydrophobic delivery carrier of the present invention may be water-insoluble. The hydrophobic delivery carrier of the present invention may comprise a wax, a polymer or a combination thereof. Waxes may be thermoplastic. Suitable waxes which may be used for the hydrophobic delivery carrier may comprise microcrystalline wax or a combination of wax and a polymer. Examples of microcrystalline wax include the Multiwax series from Sonneborn (Parsippany, N.J.), Crompton (Witco); these include Multiwax 835, Multiwax 440, Multiwax 180, and mixtures thereof. A suitable polymer which may be combined to form the hydrophobic delivery carrier may be for example polyethylene. Examples of polyethylene include A-C 1702 or A-C 6702 made by Honeywell 25 Corp. (Morristown, N.J.), with a penetration value of about 98.5 and about 90.0, respectively, under ASTM D-1321; polyethylene Performalene series from Baker Hughes; this includes polyethylene Performalene 400 from Baker Hughes Inc. (Houston, Tex.). For example, a ratio of weight percent of polymer divided by the weight percent of wax may be from about 0.01 to about 100, from about 0.1 to about 10, from about 0.5 to about 2. Examples for the hydrophobic delivery carrier of the present invention are waxes, for example the casting waxes supplied by Freeman Manufacturing Company, Ohio, USA, for example those listed in the following table or a combination thereof.

| Supplier reference number | Thickness (Gauge) | Average thickness mm +/−10% |
|---|---|---|
| 114024 | 14 | 1.58 |
| 114026 | 18 | 1.02 |
| 114007 | 20 | 0.86 |
| 114009 | 24 | 0.51 |
| 114010 | 26 | 0.39 |
| 114011 | 28 | 0.30 |
| 114012 | 30 | 0.25 |

These wax sheets are moldable and readily conform to the shape of a dental arch or tooth under manual pressure.

The delivery systems as used herein may comprise an adhesion means, such that they are capable of adhesion to oral surfaces, especially the teeth. This adhesion means may be provided by the present articles herein or the adhesion means may be provided independently of the articles herein (for example the adhesion means may be a separate phase from the articles herein where the articles may also have an adhesive means). The hydrophobic delivery carrier may be easily removed from the oral surfaces without the use of an instrument, a chemical solvent or agent or excess friction.

The hydrophobic delivery carrier may be held in place on the oral surface by adhesive means and/or attachment provided by the hydrophobic delivery carrier itself. For example, the hydrophobic delivery carrier can extend, attach, and adhere to the oral soft tissue. In addition, an adhesive can be applied to that portion of the hydrophobic delivery carrier that may attach the article to the oral soft tissue. The hydrophobic delivery carrier may also be attached to the oral cavity by physical interference or mechanical inter-locking between the hydrophobic delivery carrier and the oral surfaces including the teeth. In addition, the hydrophobic delivery carrier may be held in place by an adhesion means that is independent of the article of the present inventions herein, as disclosed in WO 03/015656.

Suitable adhesion means are known to the skilled person. When the adhesive means, if present, is provided by an adhesive, the adhesive may be any adhesive which may be used to adhere materials to the tooth surface or to a surface of the oral cavity surfaces. Suitable adhesives include, but are not limited to, skin, gum and muco adhesives, and should be able to withstand the moisture, chemicals and enzymes of the oral environment for long enough for the oral care actives and/or bleach to take effect, but may be soluble and/or biodegradable thereafter. Suitable adhesives may for example comprise water soluble polymers, hydrophobic and/or non-water-soluble polymers, pressure and moisture sensitive adhesives, e.g. dry adhesives which become tacky upon contact with the mouth environment, e.g. under the influence of moisture, chemicals or enzymes etc. in the mouth. Suitable adhesives include natural gums, synthetic resins, natural or synthetic rubbers, those gums and polymers listed above under "Thickening Agents", and various other tacky substances of the kind used in known adhesive tapes, those known from U.S. Pat. No. 2,835,628.

Solid Hydrophilic Particles

The present articles comprise a safe and effective amount of solid hydrophilic particles. The solid hydrophilic particles comprise an oral care active agent as disclosed herein. For example, the amount of solid hydrophilic particles in the article may be from about 0.01% to about 50%, or from about 0.1% to about 30%, or from about 0.2% to about 25%, by weight of the article.

In one aspect, it has been surprisingly found that better efficacy results may be achieved if the solid hydrophilic particles are located heterogeneously in the hydrophobic delivery carrier, for example higher amounts are located at a surface of the article that is intended to contact the surface of the oral cavity to be treated, and lower amounts are located at the surface on the far side. Thus, the number of the solid hydrophilic particles per cm2 may be a factor to decrease oral/topical irritation, and/or increase efficacy during use. Without wishing to be bound by theory the heterogeneous distribution focuses the oral care active agent at the intended site of action thereby reducing the amount of oral care active agent and the unintended and sometimes negative side effects. Accordingly, if the size or number of solid hydrophilic particles is too large it may lead to large spots on oral/topical/tooth surfaces that are exposed to a high concentration of the oral care active agent, which in turn may lead to oral/topical irritation and/or tooth-sensitivity and if the size or number of solid hydrophilic particles is too low efficacy may be too low. The number of solid hydrophilic particles per cm2 at the first surface may be at least 5, or from about 5 to about 10000, or from about 10 to about 1000, or from about 10 to about 100.

The number of solid hydrophilic particles at the second surface may be lower than at the first surface. Generally, for a given particle size, the lower the number of solid hydrophilic particles at the second surface the better, as more oral care active agent is concentrated at the intended side and less oral care active agent is released towards the unintended parts of the oral cavity. For example, the average number of the solid hydrophilic particles per cm2 at the second surface may be at most 200, or from about 0.01 to about 100, or from 1 to about 10.

The size of the individual solid hydrophilic particle may be a factor to decrease oral/topical irritation, or increase the intended effect, such as bleaching efficacy, when a bleaching agent is used as an oral care active agent. Without being bound by theory, if the size of the solid hydrophilic particles is too large it may lead to large spots on oral/topical/tooth surfaces that are exposed to a high concentration of the oral care active agent, which in turn may lead to oral/topical irritation and/or tooth-sensitivity. For example, the number-average equivalent-diameter or the volume-average equivalent-diameter of the solid hydrophilic particles may be from about 0.001 microns to about 5000 microns, or from about 0.01 microns to about 2000 microns, or 1 micron to about 1000 microns. The number-average equivalent-diameter or volume-average equivalent diameter of the solid hydrophilic particles can be measured according to methods and equipment known in the art, such as those from Malvern Panalytical Ltd. (e.g. Malvern Mastersizer 3000 particle size analysis equipment) or Horiba Ltd. (e.g. laser based particle size analysis equipment).

The article of the present invention comprises solid hydrophilic particles embedded in the solid hydrophobic delivery carrier. The solid hydrophilic particles may become flattened during the embedding process into the hydrophobic delivery carrier. In one aspect, the particles may be pressed into an irregular disc-like shape during the embedding process. Thereby, the surface area of the solid hydrophilic particle which is exposed to the external environment (e.g. the surface area of the solid hydrophilic particle at the first surface of the hydrophobic delivery carrier) may be increased, potentially leading to more active being released, and higher efficacy. This positive effect may be negatively affected, if the thickness of the hydrophobic delivery carrier is too large. In one aspect, it has surprisingly been found that the ratio of the average thickness of the hydrophobic delivery carrier and/or the article divided by the number-average equivalent-diameter or the volume-average equivalent-diameter of the solid hydrophilic particles may help boost the efficacy of the oral care active agent. For example, the ratio of the average thickness of the hydrophobic delivery carrier and/or the article to the number-average equivalent-diameter or the volume-average equivalent-diameter of the solid hydrophilic particles may be from about 0.001 to about 1000, from about 0.01 to about 100, or from about 0.1 to about 10.

In articles wherein the solid hydrophilic particles are embedded in the hydrophobic delivery carrier, the configuration of the embedded particles (for example shape or location) may be a factor to ensure that: 1) the embedded particles do not get detached from the hydrophobic delivery carrier during storage, shipping or handling, and/or 2) the embedded particles release an effective amount of the oral care active agent during use. Specifically, in articles wherein the solid hydrophilic particles are embedded in the hydrophobic delivery carrier, if the embedded particles are configured such that a large portion (more than about 50% for example) of the embedded particle is above the surface of the hydrophobic delivery carrier, the embedded particle may get detached from the hydrophobic delivery carrier during storage, shipping, or handling. Furthermore, if a large portion of the embedded particle protrudes above the surface of the hydrophobic delivery carrier, it may increase the roughness of the surface (for example similar to sand-paper in appearance or texture) and give the impression that it could lead to discomfort to sensitive oral tissues even before the consumer uses it, or may even poke into sensitive oral tissues during application or use and lead to discomfort. In this aspect, it is preferred that less than about 50%, or less than about 40%, or less than about 30%, or less than about 20%, of the volume of the embedded solid hydrophilic particles is disposed above the surface of the hydrophobic delivery carrier.

In addition, if embedded particles are configured such that a large portion (more than 50% for example) of the embedded particle is below the surface of the hydrophobic delivery carrier and not exposed directly to the external environment, it may not release an effective amount of the oral care active agent. In one aspect, it has been surprisingly found that in articles wherein the solid hydrophilic particles are embedded in the hydrophobic delivery carrier, the embedded particles may be configured such that 1) a large portion of the embedded particle is below the surface of the hydrophobic delivery carrier, and, 2) a large portion of the surface of the embedded particle is exposed directly to the external environment. This counterintuitive configuration of properties may 1) inhibit the embedded particles from getting detached from the hydrophobic delivery carrier, and, 2) release an effective amount of the oral care active agent from the embedded particles. For example, when particles are embedded into the hydrophobic delivery carrier by distributing the particles on a surface of the hydrophobic delivery carrier and pressing the particles into the hydrophobic delivery carrier at a high pressure (for example in a hydraulic press, between two rollers, or between a roller and a hard surface), 1) a large portion of the particle may get disposed below the surface, and 2) the particle itself may get at least partially flattened at or near the surface of the hydrophobic delivery carrier such that a large portion of the surface of the particle is exposed directly to the external environment leading to the release of an effective amount of the oral care active agent.

In articles wherein the solid hydrophilic particles are embedded in the hydrophobic delivery carrier, 1) more than about 50%, or more than about 75%, or more than about 95%, or 100% of the volume of the embedded particles may be disposed below or at the surface of the hydrophobic delivery carrier, and/or 2) more than about 10%, or more than about 20%, or more than about 30% of the surface area of the embedded particles is disposed at the surface of the hydrophobic delivery carrier and thereby exposed directly to the external environment surrounding the hydrophobic delivery carrier.

The size of the solid hydrophilic particles, thickness of the solid hydrophobic delivery carrier, or pressure applied may influence the configuration (for example shape or location) of the embedded particles. Solid hydrophilic particles may be embedded in the hydrophobic delivery carrier by distributing the particles on a surface of the hydrophobic delivery carrier and pressing the particles into the delivery carrier at a pressure of at least about 50 pounds per square inch (PSI), or at least about 500 PSI, or at least about 5000 PSI, or at least about 50,000 PSI, or from about 50 PSI to about 50,000 PSI, or from about 50 PSI to about 5000 PSI, or from about 500 PSI to about 5000 PSI.

The oral care active agent per solid hydrophilic particle may be from about 1% to about 95%, or from about 10% to about 50%, or from about 15% to about 40% by weight of the solid hydrophilic particles.

It has been surprisingly found that the level of the oral care active agent required to achieve the intended effect in the present invention is surprisingly low, by weight of the article, for example lower than concentrations of active agents usually used in previous commercial products. For example, the concentration of oral care active agent may be from about 0.001% to about 25%, or from about 0.01% to about 15%, or from about 0.01% to about 10%, or from about 0.01% to about 5%, or from about 0.01% to about 3%, by weight of the article.

The article of the present invention can comprise several different oral care active agents as disclosed herein. The level of some active agents may be regulated and/or limited due to regulatory requirements. For example, if a bleaching agent is used as active agent a suitable level of the active agent is not only calculated according to the intended effect, but also has to meet the regulatory requirements. For example, a suitable overall concentration of bleaching agents as active agents may be less than 0.1%, from about 0.01% to about 0.099995%, from about 0.01% to about 0.095%, from about 0.05% to about 0.09%. Bleaching agents provided by the solid hydrophilic particles can be effective when used even at very low levels in the articles as disclosed herein. If higher levels of bleaching agents are used, e.g. up to about 3% by weight of the article, the overall concentration of bleaching agents as active agents may be less than about 3% by weight of the article, or from about 0.1% to about 3%, or from about 0.5% to about 3% by weight of the article.

Without wishing to be bound by theory it is believed that the surprisingly high efficacy delivered by extremely low concentrations of oral care active agents is achieved by the direct delivery of the oral care active agent at the surface in need of the treatment. Accordingly, the concentration of the oral care active agent at the first surface (which generally is the surface of the article that is intended to contact the surface of the oral cavity to be treated) can be measured. For example, the concentration of the at least one oral care active agent at the first surface may be in the range from about 1 microgram/cm2 to about 10000 micrograms/cm2, or from about 10 micrograms/cm2 to about 5000 micrograms/cm2, or from about 50 micrograms/cm2 to about 3000 micrograms/cm2, as measured according to the method specified herein.

The concentration of the oral care active agent at the second surface of the article (which generally is opposite the first surface), may be significantly lower than the concentration at the first surface. For example, the concentration of the at least oral care one active agent at the second surface may be from about 0.001 micrograms/cm2 to about 500 micrograms/cm2, or from about 0.01 micrograms/cm2 to about 200 micrograms/cm2, or from about 0.1 micrograms/cm2 to about 100 micrograms/cm2, as measured according to the method specified herein.

The ratio of the concentration of the oral care active agent or bleaching agent at the first surface to the concentration of the oral care active agent or bleaching agent at the second surface, as measured according to the procedure specified herein, may be greater than 1, or from about 2 to about 10000, or from about 2 to about 1000, or from about 2 to about 100.

In one aspect, it has been surprisingly found that the solubility of the solid hydrophilic particles in water, the ability to swell upon contact with water, or the ability to release an oral care active agent upon contact with water, may impact the efficacy of the article. For example, at least about 20, 25, 30, 40, 50, 60, 70, or 80 parts by weight of the solid hydrophilic particles may dissolve in about 100 parts by weight of water; and/or the solid hydrophilic particles may swell by at least about 20%, 25%, 30%, 40%, 50%, 60%, 70%, or 80% upon contact with water. The amount of water available on the facial surface of the maxillary anterior teeth to hydrate the solid hydrophilic particles and release the active ingredients tends to be low compared to the rest of the oral cavity. This may be especially important because the facial surfaces of the maxillary anterior teeth are the ones that are most visible when smiling. Thus, the solubility of the solid hydrophilic particles in water, its ability to swell upon contact with water, or its ability to release an oral care active agent upon contact with water can impact the efficacy of the article disproportionately on the "smile teeth" (facial surface of the maxillary anterior teeth). In this regard, the first surface of the solid deliver carrier of the article may be applied to the facial surfaces of the maxillary anterior teeth of the user of the article.

The solid hydrophilic particles are insoluble in the hydrophobic delivery carrier of the present invention.

Active Agents for Oral Care

The article of the present invention comprises a safe and effective amount of at least one active agent for oral care. Suitable oral care active agents include any material that is generally considered safe for use in the oral cavity and that provides changes to the overall appearance and/or health of the oral cavity. For example suitable oral care actives may include one or more bleaching agent(s), tooth whitening agent(s), healing agent(s), anticalculus agent(s), fluoride ion source(s), antimicrobial agent(s), remineralization agent(s), dentinal desensitizing agent(s), anesthetic agent(s), antifungal agent(s), coolants, anti-inflammatory agent(s), selective H-2 antagonist(s), anticaries agent(s), nutrient(s), erythritol, probiotics, resolvins including eicosapentaenoic acid (EPA) and docosahexaenoic acid (DHA), as well as docosapentaenoic acid (DPA) clupanodonic acid, Resolvin D's RvD1 (7S,8R,17S-trihydroxy-DHA), RvD2 (7S,16R,17S-trihydroxy-DHA), RvD3 (4S,7R,17S-trihydroxy-DHA), RvD4 (4S,5,17S-trihydroxy-DHA), RvD5 (7S,17S-dihydroxy-DHA), and RvD6 (4S,17S-dihydroxy-DHA) and Resolvin E's: RvE1 (5S,12R,18R-trihydroxy-EPA), 18S-Rv1 (5S, 12R,18S-trihydroxy-EPA), RvE2 (5S,18R-dihydroxy-EPA), and RvE3 (17R,18R/S-dihydroxy-EPA), tranexamic acid, glycine, retinol, amino acids, such as for example histidine, isoleucine, leucine, lysine, methionine, phenylalanine, threonine, tryptophan, valine, alanine, asparagine, aspartic acid, glutamic acid, arginine, cysteine, glutamine, tyrosine, glycine, ornithine, proline, and serine, peptides, calcium salts of amino acids and peptides, niacinamide, human growth factors, and mixtures and/or combinations thereof. The solid hydrophilic particle may contain at least one oral care active agent at a level where upon directed use, the intended benefit is promoted without detriment to the oral surface to which it is applied. Examples of the oral conditions these actives address include, but, are not limited to, appearance and structural changes to teeth, for example reducing and/or removing, caries, plaque, tartar and stain, providing antibacterial effects, cavity prevention and treatment, treatment of inflamed and/or bleeding gums, mucosal wounds, lesions, ulcers, aphthous ulcers, cold sores, tooth abscesses, the elimination of mouth malodor and improving breath resulting from the conditions above and other causes, such as microbial proliferation.

For example, the oral care active agent may be a healing agent that promotes or enhances the healing or regenerative process. Such healing agents may comprise hyaluronic acid or salts, glucosamine or salts, allantoin, curcumin, D panthenol, niacinamide, ellagic acid, flavonoids (including fisetin, quercetin, luteolin, apigenin), vitamin E, ubiquinone, or mixtures thereof.

The oral care active agent may be one or more anti-inflammatory agent(s) including, but not limited to, non-steroidal anti-inflammatory agents such as acetyl salicylic acid, ketorolac, flurbiprofen, ibuprofen, naproxen, indomethacin, acetaminophen, acetyl salicylic acid, steroids, ketorolac, naproxen, ketoprofen, piroxicam and meclofenamic acid, COX-2 inhibitors such as valdecoxib, celecoxib and rofecoxib, and mixtures thereof. If present, the anti-inflammatory agents generally comprise from about 0.001% to about 5% by weight of the articles.

The oral care active agent may be one or more probiotics selected from Lactobacillus reuteri ATCC 55730; Lactobacillus salivarius strain T112711 (LS 1); Lactobacillus paracasei ADP-1; Streptococcus salivarius K12; Bifidobacterium DN-173 010; Filtrate of L. paracasei strain (Pro-t-Action™); S. Oralis KJ3, S. rattus JH145, S. uberis KJ2; Lactobacillus, reuteri Prodentis; Lactobacillus salivarius LS1; Lactobacillus paracasei; Lactobacillus paracasei ADP1; Streptococcus salivarius M18, K12 or BUS K12 and BUS M18; Bacillus Amyloliquefaciens; Bacillus Clausii; Bacillus Coagulans; Bacillus Subtilis; Bacillus subtilis: E-300; Bifidobacterium Animalis; Bifidobacterium B6; Bifidobacterium Bifidum; Bifidobacterium Breve (Bb-03); Bifidobacterium DN-173 010; Bifidobacterium GB1 30 6068; Bifidobacterium infantis; Bifidobacterium Lactis; Bifidobacterium lactis Bb-12; Bifidobacterium Longum; Bifidobacterium Thermophilum; Enterococcus Faecalis; Enterococcus Faecium; Enterococcus Faecium NCIMB 10415; Enterococcus LAB SF 68; Lactobacilli reuteri ATCC 55730 and ATCC PTA 5289; Lactobacilli reuteri ATCC 55730 and ATCC PTA 5289 (10:1); Lactobacillus Acidophilus; Lactobacillus acidophilus ATCC 4356 and Bifidobacterium bifidum ATCC 29521; Lactobacillus acidophilus; Bifidobacterium longum; Bifidobacterium bifidum; Bifidobacterium lactis; Lactobacillus Brevis; Lactobacillus Casei (subsp. Casi); Lactobacillus casei Shirota; Lactobacillus Confusus; Lactobacillus crispatus YIT 12319; Lactobacillus Curvatus; Lactobacillus Delbrueckii Ssp. Bulgaricus PXN 39; Lactobacillus Fermentum; Lactobacillus fermentum YIT 12320; Lactobacillus Gasseri; Lactobacillus gasseri YIT 12321; Lactobacillus Helveticus; Lactobacillus Johnsonii; Lactobacillus Kimchii; Lactobacillus Lactis L1A; Lactobacillus Paracasei (Lpc37); Lactobacillus paracasei GMNL-33; Lactobacillus Pentosus; Lactobacillus plantarum; Lactobacillus Plantarum; Lactobacillus Protectus; Lactobacillus Reuteri; Lactobacillus reuteri ATCC 55730; Lactobacillus reuteri SD2112 (ATCC55730); Lactobacillus Rhamnosus (GG); Lactobacillus rhamnosus GG; Lactobacillus rhamnosus GG; L. rhamnosus LC705; Propionibacterium freudenreichii ssp; shermanii JS; Lactobacillus rhamnosus L8020; Lactobacillus rhamnosus LB21; Lactobacillus Salivarius; Lactobacillus salivarius WB21; Lactobacillus Sporogenes; Lactococcus Lactis Ssp Diacetylactis; Lactococcus Lactis Ssp. Lactis; Pediococcus Acidilactici; Pediococcus Pentosaceus; Saccharomyces Boulardii; Saccharomyces Cerevisiae; Strep. uberis KJ2sm; Strep. oralis KJ3sm; trep. rattus JH145; Streptococcus mitis YIT 12322; Streptococcus Oralis KJ3; Streptococcus Rattus JH145; Streptococcus Salivarius (BUIS K12 or BUS M18); Streptococcus salivarius K12; Streptococcus Thermophilus; Streptococcus Uberis KJ2; Thermus thermophiles; Weissella cibaria CMS2; Weissella cibaria CMS3; and Weissella cibaria CMU.

Probiotics can be used in the articles of the present invention to promote positive oral health effects, such as reduce caries and plaque, promote gum health, improve breath, and promote whitening. The efficacy of probiotics in the articles can be determined for example by measuring one or more of the following: reduction of the levels of salivary *mutans* streptococci; reduction of gingival crevicular fluid; reduction of periodontal pathogens (*C. rectus* and *P. gingivitis*) in subgingival plaque; decreased counts of yeast; decreased prevalence of oral *candida*; reduction of oral volatile sulfur compound (VSC) levels; and reduction of TNF-α and IL-8 production. Without being limited to theory it is believed that one or more of the above positive oral health effects may be achieved through the production of bacterial toxins, which remove or reduce certain types of bacteria in the oral cavity; further one or more of the above positive oral health effects may be achieved through bacterial production of one or more enzymes that inhibit the production of or dissolves/loosens biofilms or sticky deposits that can lead to oral health problems.

For example, at least one anti-calculus agent may be used in the articles as disclosed herein. The anticalculus agent may be selected from the group consisting of polyphosphates and salts thereof; polyamino propane sulfonic acid (AMPS) and salts thereof; polyolefin sulfonates and salts thereof; polyvinyl phosphates and salts thereof; polyolefin phosphates and salts thereof; diphosphonates and salts thereof; phosphonoalkane carboxylic acid and salts thereof; polyphosphonates and salts thereof; polyvinyl phosphonates and salts thereof; polyolefin phosphonates and salts thereof; polypeptides; and mixtures thereof, wherein the mentioned salts are usually alkali metal salts. For example anticalculus agents, such as pyrophosphates, polyphosphates, polyphophonates and mixtures thereof, may also show a stabilizing effect to the solid hydrophilic oral care active agents, for example if a bleaching agent will be used as the active agent.

The anticalculus agent may be for example a polyphosphate. A polyphosphate is generally understood to comprise two or more phosphate molecules arranged primarily in a linear configuration, although some cyclic derivatives may be present. Linear polyphosphates correspond to $(X\ PO_3)_n$ where n is about 2 to about 125, wherein preferably n is greater than 4, and X is for example sodium, potassium, etc. For $(X\ PO_3)_n$ when n is at least 3 the polyphosphates are glassy in character. Counter-ions for these phosphates may be the alkali metal, alkaline earth metal, ammonium, $C_2$-$C_6$ alkanolammonium and salt mixtures. Polyphosphates are generally employed as their wholly or partially neutralized water-soluble alkali metal salts such as potassium, sodium, ammonium salts, and mixtures thereof. The inorganic polyphosphate salts include alkali metal (e.g. sodium) tripolyphosphate, tetrapolyphosphate, dialkyl metal (e.g. disodium) diacid, trialkyl metal (e.g. trisodium) monoacid, potassium hydrogen phosphate, sodium hydrogen phosphate, and alkali metal (e.g. sodium) hexametaphosphate, and mixtures thereof. Polyphosphates larger than tetrapolyphosphate usually occur as amorphous glassy materials, such as those manufactured by FMC Corporation which are commercially known as Sodaphos (n≈6), Hexaphos (n≈13), Glass H (n≈21), and mixtures thereof. The level of polyphosphates in the present articles may be from about 1.5% to about 10%, for example from about 2% to about 10%, or from about 6% to about 10%, by weight of the article.

The pyrophosphate salts useful in the present articles include, alkali metal pyrophosphates, di-, tri-, and monopotassium or sodium pyrophosphates, dialkali metal pyrophosphate salts, tetraalkali metal pyrophosphate salts, and mixtures thereof. For example, the pyrophosphate salt may be selected from the group consisting of trisodium pyrophosphate, disodium dihydrogen pyrophosphate ($Na_2H_2P_2O_7$), dipotassium pyrophosphate, tetrasodium pyrophosphate ($Na_4P_2O_7$), tetrapotassium pyrophosphate ($K_4P_2O_7$), and mixtures thereof, wherein tetrasodium pyrophosphate is preferred. Tetrasodium pyrophosphate may be the anhydrous salt form or the decahydrate form, or any other species stable in solid form in the present articles. The salt is in its solid particle form, which may be its crystalline and/or amorphous state, with the particle size of the salt preferably being small enough to be aesthetically acceptable and readily soluble during use. The level of pyrophosphate salt in the present articles may be from about 1.5% to about 10%, for example from about 2% to about 10%, ory from about 3% to about 8%, by weight of the article. The phosphate sources, including but are not limited to, polyphosphates and pyrophosphates, are described in more detail in Kirk & Othmer, Encyclopedia of Chemical Technology, Fourth Edition, Volume 18, Wiley-Interscience Publishers (1996), pages 685-707.

Polyolefin phosphonates include those wherein the olefin group contains 2 or more carbon atoms. Polyvinylphosphonates include polyvinylphosphonic acid. Diphosphonates and salts thereof include azocycloalkane-2,2-diphosphonic acids and salts thereof, ions of azocycloalkane-2,2-diphosphonic acids and salts thereof (such as those which the alkane moiety has five, six or seven carbon atoms, in which the nitrogen atom is unsubstituted or carries a lower alkyl substitutent, e.g. methyl), azacyclohexane-2,2-diphosphonic acid, azacyclopentane-2,2-diphosphonic acid, N-methyl-azacyclopentane-2,3-diphosphonic acid, EHDP (ethanehydroxy-1,1,-diphosphonic acid), AHP (azacycloheptane-2,2-diphosphonic acid, a.k.a. 1-azocycloheptylidene-2,2-diphosphonic acid), ethane-1-amino-1,1-diphosphonate, dichloromethane-diphosphonate, etc. Phosphonoalkane carboxylic acid or their alkali metal salts include PPTA (phosphonopropane tricarboxylic acid), PBTA (phosphonobutane-1,2,4-tricarboxylic acid), each as acid or alkali metal salts.

Antimicrobial antiplaque agents may be used as suitable oral care active agents of the present invention and may include, but are not limited to, triclosan, hops acids from hops extracts, such as hops alpha acids, including, humulone, adhumulone, cohumulone, posthumulone, prehumulon, and combinations thereof, or hops beta acids, including, lupulone, adlupulone, colupulone, and combinations thereof, 5-chloro-2-(2,4-dichlorophenoxy)-phenol, as described in The Merck Index, 11th ed. (1989), pp. 1529 (entry no. 9573) in U.S. Pat. No. 3,506,720, and in European Patent Application No. 0,251,591; chlorhexidine (Merck Index, no. 2090), alexidine (Merck Index, no. 222; hexetidine (Merck Index, no. 4624); sanguinarine (Merck Index, no. 8320); benzalkonium chloride (Merck Index, no. 1066); salicylanilide (Merck Index, no. 8299); domiphen bromide (Merck Index, no. 3411); cetylpyridinium chloride (CPC) (Merck Index, no. 2024; tetradecylpyridinium chloride (TPC); N-tetradecyl-4-ethylpyridinium chloride (TDEPC); octenidine; delmopinol, octapinol, and other piperidino derivatives; cocomidyl propyl betaine, sodium cocomidyl glutamate, sodium lauryl sarcosinate, GTF inhibitors, povidone iodine delmopinol, propolis, phthalic acid and its salts, monoperthalic acid and its salts and esters, ascorbyl stearale, oleoyl saicosine, alkyl sulfate. The articles may comprise effective antimicrobial amounts of essential oils, herbal extracts, and combinations thereof for example citral, geranial, rosemary extract, tea extract, magnolia extract, eucalyptol geraniol, carvacrol, citral, hinokitol, catechol, methyl salicylate, epigallocatechin gallate, epigallocatechin. gallic acid, miswak extract, sea-buckthorn extract, and combinations of menthol, eucalyptol, thymol and methyl salicylate;

antimicrobial metals and salts thereof; for example those providing zinc ions, stannous ions, copper ions, and/or mixtures thereof; bisbiguanides, or phenolics; antibiotics such as augmentin, amoxicillin, tetracycline, doxycycline, minocycline, and metronidazole; and analogs and salts of the above antimicrobial antiplaque agents and/or anti-fungals such as those for the treatment of *Candida albicans*. If present, these oral care active agents generally are present in a safe and effective amount for example from about 0.1% to about 5% by weight of the present articles.

In another aspect, anticaries agent(s) may be a suitable oral care active agent for the articles of the present invention. The anticaries agent may be selected from the group consisting of fluoride, sodium fluoride, potassium fluoride, titanium fluoride, hydrofluoric acid, amine fluoride, sodium monofluorophosphate, ammonium fluoride, stannous fluoride, stannous chloride, stannous gluconate, copper salts, copper chloride, copper glycinate, zinc chloride, zinc lactate, zinc citrate, zinc phosphate, sodium iodide, potassium iodide, calcium chloride, calcium lactate, calcium phosphate, hydroxyapatite, fluoroapatite, amorphous calcium phosphate, crystalline calcium phosphate, sodium bicarbonate, sodium carbonate, calcium carbonate, oxalic acid, dipotassium oxalate, monosodium monopotassium oxalate, casein phosphopeptides, casein phosphopeptide coated hydroxy apatite, bioglass containing one or more of $SiO_2$, $CaO$, $Na_2O$, $P_2O_5$, $CaF_2$, $B_2O_3$, $K_2O$, $MgO$, such as those disclosed in U.S. Pat. No. 5,735,942. If present, the instant articles provide from about 50 ppm to 10,000 ppm, or from about 100 to 3000 ppm, of fluoride ions in the articles as disclosed herein.

Nutrients, such as minerals, may improve the teeth and the tooth surface and thus may be used as suitable oral care active agent with the articles as disclosed herein. Suitable minerals are e.g. calcium, phosphorus, fluoride, zinc, manganese, potassium and mixtures thereof. These minerals are e.g. disclosed in Drug Facts and Comparisons (loose leaf drug information service), Wolters Kluer Company, St. Louis, Mo., ©1997, pp 10-17.

Bleaching Agents

The solid hydrophilic particles may comprise bleaching agents as the oral care active agent and may deliver hydrogen peroxide as an adduct or complex of hydrogen peroxide, or precursor to hydrogen peroxide. Examples of hydrophilic bleaching agent particles include agents that provide bleaching effects, stain bleaching effects, stain removal effects, stain color change effects or any other effect, which change, or brighten tooth color. For example, hydrophilic bleaching agent particles include a source of peroxide radicals. Hydrophilic bleaching agent particles may include peroxides, metal chlorites, perborates, percarbonates, peroxyacids, persulfates, compounds that form the preceding compounds in situ, and combinations thereof. Examples of peroxide compounds may include urea peroxide (also known as carbamide peroxide or urea hydrogen peroxide adduct), calcium peroxide, and mixtures thereof. Examples of metal chlorites may include calcium chlorite, barium chlorite, magnesium chlorite, lithium chlorite, sodium chlorite, potassium chlorite, and mixtures thereof. Examples of hydrophilic bleaching agent particles may include hypochlorites (such as metal hypochlorites). Examples of persulfates may include salts of peroxymonosulfate, peroxydisulfate and mixtures thereof. Examples of persulfates perborates, percarbonates, and hypochlorites include corresponding salts of sodium, calcium, potassium, and other metals. Examples of solid hydrophilic bleaching agent particles include, but are not limited to complexes of hydrogen peroxide and polyvinylpyrrolidone (PVP) polymers (also known as Peroxydone), urea peroxide, and mixtures thereof.

As such, the articles as disclosed herein deliver a high ratio of the concentration in weight percent of the active agent, such as hydrogen peroxide present in the solid hydrophilic particles, to the concentration in weight percent of active agent, present in the overall article. This results from the high concentration in weight percent of active agent present in the solid hydrophilic particles combined with a relatively low concentration in weight percent of active agent present in the overall article. Without being bound by theory, in aspects of the present invention comprising hydrogen peroxide, this surprising combination of seemingly contradictory parameters delivers the hydrogen peroxide to the tooth surface with a high driving force even when the overall concentration or amount of hydrogen peroxide delivered to the tooth surface is low. As a result, the high driving force delivers a surprisingly high level of bleaching efficacy and/or bleaching speed; while the low overall concentration or low amount of bleaching agent delivered to the tooth surface may help reduce tooth sensitivity. For example, the ratio of the concentration in weight percent of active agent present in the solid hydrophilic particles to the concentration in weight percent of active agent present in the overall article may be from about 2 to about 50000, or from about 3 to about 10000, or from about 5 to about 1000.

The oral care active agents of the present invention may be stabilized against degradation by the shielding effect of the hydrophobic delivery carrier. Further stabilizing agents for the active agent may be present in the articles as disclosed herein. Active agents for example bleaching agents may be further stabilized against degradation by the article. Therefore, stabilizing agents may be added to the present article. Suitable stabilizing agents are for example ortho-phosphoric acid, phosphate(s), such as sodium hydrogen phosphate, pyrophosphate(s), organophosphonate(s), Ethylenediaminetetraacetic acid, Ethylenediamine-N,N'-diacetic acid, Ethylenediamine-N,N'-disuccinic acid, potassium stannate, sodium stannate, tin salts, zinc salts, salicylic acid, 1-Hydroxyethylidene-1,1-diphosphonic acid, and combinations thereof. For example, stabilizers may be used which show additional oral care effects, such as anti-tartar effect, produced by phosphates as disclosed herein, for example pyrophosphate, tripolyphosphate, hexametaphosphate, phytic acid, salts of $PO_3(PO2)_nPO3$ where n=2-30, phosphoric acid, gantrez, zinc salts including zinc citrate, zinc lactate, zinc chloride, zinc phosphate, zinc oxide, enzymes such as dextransess, xylanases, proteases, phosphonates such as bis-phosphonate, chelants such as EDTA, Calcium Sodium EDTA, Citrate, citric acid, oxalic acid, oxalate salts, polymers (such as those disclosed in U.S. application Ser. No. 16/216,329), PVP, polyacrylic acid (carbopol), polyacrylates, stannous salts, stannic salts. A stabilizing agent may be present in an article of the present invention in an amount from about 0.0000001%, 0.000001%, or 0.00001%, to about 0.00001%, 0.0001%, or 0.01% by weight of the article. For example, a stabilizing agent may be present in an article of the present invention in an amount from about 0.0001%, or 0.01% to about 0.01%, 0.1% or about 1% by weight of the solid hydrophilic particles.

A stabilizing agent may also include chelants. The chelant may be a copper, iron and/or manganese chelants, or a mixture thereof. Suitable chelants may be selected from: diethylene triamine pentaacetate, diethylene triamine penta (methyl phosphonic acid), ethylene diamine-N'N'-disuccinic acid, ethylene diamine tetraacetate, ethylene diamine tetra (methylene phosphonic acid), hydroxyethane di(methylene phosphonic acid), and any combination thereof. A suitable chelant may be selected from ethylene diamine-N'N'-disuccinic acid (EDDS), hydroxyethane diphosphonic acid (HEDP) or mixtures thereof. The stabilizer may comprise ethylene diamine-N'N'-disuccinic acid or salt thereof. The ethylene diamine-N'N'-disuccinic acid may be in S,S enantiomeric form. The stabilizer may comprise 4,5-dihydroxy-m-benzenedisulfonic acid disodium salt, glutamic acid-N,N-diacetic acid (GLDA) and/or salts thereof, 2-hydroxypyridine-1-oxide, Trilon P™ available from BASF, Ludwigshafen, Germany. Suitable chelants may also be calcium carbonate crystal growth inhibitors, such as 1-hydroxyethanediphosphonic acid (HEDP); N,N-dicarboxymethyl-2-aminopentane-1,5-dioic acid; 2-phosphonobutane-1,2,4-tricarboxylic acid; and salts thereof; and any combination thereof. A stabilizer may comprise a hydroxamate chelant, such as hydroxamic acid or a corresponding salt, for example coco hydroxamic acid (Axis House RK 853).

The article as disclosed herein may comprise optional additional ingredients. For example, a further optional ingredient may be present in the article which is intended to be released from the second side, e.g. the far side of the hydrophobic delivery carrier. For example coolants, desensitizing agents, numbing agents and/or taste and/or aesthetics improving agent(s), such as flavoring agents can be used as optional ingredients in articles of the present invention, for example at a level of from about 0.001% to about 10%, or from about 0.1% to about 1%, by weight of the article. Coolants, desensitizing agents and numbing agents may decrease potential negative perceptions, such as tingling, burning etc. provoked by an active agent such as a bleaching agent. A wide variety of materials can be used as coolants, including, but are not limited to carboxamides, menthol, ketals, diols, and mixtures thereof. Optional coolants in the present articles may be the paramenthan carboxyamide agents such as N-ethyl-p-menthan-3-carboxamide (known as "WS-3"), N,2,3-trimethyl-2-isopropylbutanamide (known as "WS-23"), menthol, 3-1-menthoxypropane-1,2-diol (known as TK-10), menthone glycerol acetal (known as MGA) menthyl lactate (known as Frescolat®), and mixtures thereof. The terms menthol and menthyl as used herein include dextro- and levorotatory isomers of these compounds and racemic mixtures thereof. Desensitizing or antipain agent may include, but are not limited to, strontium chloride, potassium nitrate, natural herbs such as gall nut, *Asarum*, Cubebin, Galanga, scutellaria, Liangmianzhen, Baizhi, etc. Suitable numbing agents include benzocaine, lidocaine, clove bud oil, and ethanol.

Suitable flavoring agents include oil of wintergreen, oil of peppermint, oil of spearmint, clove bud oil, menthol, anethole, methyl salicylate, eucalyptol, 1-menthyl acetate, sage, eugenol, parsley oil, oxanone, alpha-irisone, marjoram, lemon, orange, propenyl guaethol, cinnamon, vanillin, thymol, linalool, cinnamaldehyde glycerol acetal (known as CGA), and mixtures thereof. If present the flavoring agents are generally used at levels of from about 0.01% to about 10%, for example from about 1% to about 5%, or from about 1.5% to about 2%, by weight of the article.

The present articles may optionally comprise sweetening agents including sucralose, sucrose, glucose, saccharin, dextrose, levulose, lactose, mannitol, sorbitol, fructose, maltose, xylitol, saccharin salts, thaumatin, aspartame, D-tryptophan, dihydrochalcones, acesulfame and cyclamate salts, especially sodium cyclamate and sodium saccharin, and mixtures thereof. If present, the article contains from about 0.1% to about 10% of these agents, for example from about 0.1% to about 1%, by weight of the article.

Dyes, pigments, colorants, and mixtures thereof may optionally be included in the present article to give the articles colored appearance. An advantage of adding pigments and/or colorants to the articles herein is that it will allow the user to see if the article covers their teeth evenly and completely, since coverage is easier to see with a colored article. The colorant may provide color similar to the color of bleached teeth. Colorants useful herein are stable with the active agent and are those recognized as safe. The levels of dye, pigments and colorants that are optionally used herein are in the range of about 0.001% to about 15%, for example from about 0.01% to about 10% or from about 0.1% to about 5% by weight of the article.

In one aspect, two or more oral care active agents that are normally incompatible with each other may be separately combined in the same article of the present invention. The solid hydrophobic delivery carrier can thus maintain separation of such incompatible active agents. For example, the present invention may comprise a hydrophilic bleaching agent as active agent combined with an additional oral care active agent that further improves the bleaching efficacy of the article. Examples include bleaching agents combined with additional oral care actives that may provide a driving force to increase the pH when contacted with water. Specifically, examples include solid hydrophilic particles comprising peroxides separately combined with sodium bicarbonate (baking soda) in the solid hydrophobic delivery carrier. When in contact, peroxide and baking soda are reactive towards one another, and when separately added to the solid hydrophobic delivery carrier of the present invention can be maintained separated from each other until use. While not wishing to be bound by theory it is hypothesized that particles of two or more hydrophilic oral care active agents that are normally incompatible with each other are kept substantially separated from each other in the hydrophobic delivery carrier—this separation even on a microscopic scale, may minimize or eliminate the incompatibility. Furthermore, it is hypothesized that when particles of one of the hydrophilic oral care agents come in contact with moisture, for example at the time of use in the oral cavity, the components of the particles may at least partially dissolve or swell and make direct contact with components of the particles of the other oral care agents; however, this may happen primarily at the time of use in the oral cavity, and only minimally or not at all prior to that in the article. Thus, the article of the present invention may comprise two or more oral care active agents that are normally incompatible with each other.

To the extent oral care active agents are desired to be incorporated in the solid hydrophilic particles of the present invention, but the oral care active agent is typically provided as a solid particle that has relatively low water solubility (e.g. less than about 20, or less than about 15, parts by weight of the solid particles dissolve in about 100 parts by weight of water), such oral care active agent can be solubilized in a suitable solvent (e.g. water, glycerin, or the like), then incorporated in a solid hydrophilic particle (e.g. a PVP solid hydrophilic particle), and then the resulting solid hydrophilic particle comprising the oral care active agent being incorporated into the oral care article of the present invention.

To the extent oral care active agents are desired to be incorporated in the solid hydrophilic particles of the present invention, but the oral care active agent is typically provided as a liquid material, such oral care active agent can be incorporated in a solid hydrophilic particle (e.g. a PVP solid hydrophilic particle), and then the resulting solid hydrophilic particle comprising the oral care active agent being incorporated into the oral care article of the present invention.

Identifying Indicia

The oral care articles of the present invention can further comprise identifying indicia to assist a user of the article to apply the correct side of the article to the user's teeth. The user may apply the first surface of the article (as described herein) to the teeth of user, while the second surface faces away from the user's teeth. Identifying indicia can be in the form of words, logos, trademarks, trade names, or the like, and printed or embossed on a surface of the oral care article itself or on packaging for the oral care article. Identifying indicia can also include coloring the first surface of the article a different color from the second surface of the article. As such, in one aspect, the oral care article further comprises identifying indicia to distinguish, for example visually distinguish, the first surface of the article from the second surface of the article.

Bleaching Efficacy

If a bleaching agent is used as oral care active agent, for example, the bleaching efficacy of the articles of the present invention, as measured per the clinical protocol disclosed herein and calculated as $-\Delta b^*$ may be at least at least about 0.25, or at least about 0.5, or at least about 1.0, or at least about 1.5, or at least about 2, or at least about 2.5, or at least about 3, or at least about 3.5, and or at least about 4. Generally, a change in yellowness, as measured per the clinical protocol as disclosed herein, and calculated as $-\Delta b^*$ of at least 0.25 is noticeable.

If a bleaching agent is used as active agent, for example, the present invention may deliver a surprisingly high ratio of bleaching efficacy, as measured per the clinical protocol disclosed herein, and calculated as $-\Delta b^*$, to the weight percent of bleaching agent present in the overall article. For example, a $-\Delta b^*$ of 1.5 with an article containing 3%, by weight of the article, of bleaching agent, would deliver a ratio of bleaching efficacy, as measured per the clinical protocol as disclosed herein, and calculated as $-\Delta b^*$, to the weight percent of bleaching agent present in the overall article of 0.5. If a bleaching agent is used as active agent, for example, the ratio of bleaching efficacy of the present invention, as measured per the clinical protocol disclosed herein, and calculated as $-\Delta b^*$ to the weight percent of bleaching agent present in the overall article may be, at least about 2.5, or at least about 5, or at least about 10, or at least about 15.

If a bleaching agent is used as active agent, for example, the present invention may deliver: 1) a surprisingly high ratio of bleaching efficacy, as measured per the clinical protocol as disclosed herein, and calculated as $-\Delta b^*$, to the fraction of participants who reported oral irritation or were observed to have oral irritation that was possibly or probably attributed to the article tested; 2) a surprisingly high ratio of bleaching efficacy, as measured per the clinical protocol as disclosed herein, and calculated as $-\Delta b^*$, to the fraction of participants who reported tooth sensitivity that was possibly or probably attributed to the article; or 3) a surprisingly high ratio of bleaching efficacy, as measured per the clinical protocol as disclosed herein, and calculated as $-\Delta b^*$, to the fraction of participants who reported tooth sensitivity and reported oral irritation or were observed to have oral irritation that was possibly or probably attributed to the article.

If a bleaching agent is used as active agent, for example, the ratio of bleaching efficacy of the present invention, as measured per the clinical protocol as disclosed herein, and calculated as $-\Delta b^*$, to the fraction of participants who report tooth sensitivity, oral irritation or both or are observed to have tooth sensitivity, oral irritation or both that is possibly or probably attributed to the present invention may be at least at least about 6, or at least about 8, or at least about 10, or at least about 15, or at least about 20, or at least about 25, or at least about 50.

Clinical Protocol

The bleaching efficacies of the oral compositions comprising bleaching agents as active agents are measured using the following clinical protocol. Per treatment group, 17 to 25 participants are recruited to complete the clinical study when testing oral compositions with less than about 1% bleaching agent, and 8 to 25 participants when testing oral compositions with at least about 1% bleaching agent. Recruited participants must have four natural maxillary incisors with all measurable facial sites. The mean baseline $L^*$ of the group of participants must be from 71 to 76, and the mean baseline $b^*$ of the group of participants must be from 13 to 18. In addition, participants with malocclusion on maxillary anterior teeth, severe or atypical intrinsic staining, such as that caused by tetracycline, fluorosis or hypo-calcification, dental crowns or restorations on the facial surfaces of maxillary anterior teeth, self-reported medical history of melanoma, current smoking or tobacco use, light-sensitivity or a pigmentation skin disorder, self-reported tooth sensitivity, or previous tooth whitening using a professional treatment, over-the-counter kit, or investigational product, are excluded from the study. Participants are provided with take-home kits with Crest Cavity Protection toothpaste and Oral-B Indicator soft manual toothbrush (both from Procter & Gamble, Cincinnati, Ohio, USA) to be used twice a day in the customary manner.

The participants use a toothbrush ("Anchor 41 tuft white toothbrush" from Team Technologies, Inc. Morristown, Tenn., USA) to brush their teeth with water for 30 seconds prior to being treated with the oral composition. The maxillary anterior teeth of each participant are treated with the oral composition for 60 minutes once daily. If the oral composition to be assessed is a semisolid gel, from 0.6 g to 0.8 g of the oral composition is applied across a film of clear flexible polyethylene 66 mm×15 mm in size and from about 0.01 mm to about 0.02 mm thick prior to applying to the maxillary anterior teeth. If the oral composition to be assessed is a solid article, the article is applied directly to the maxillary anterior teeth.

Figure 9:
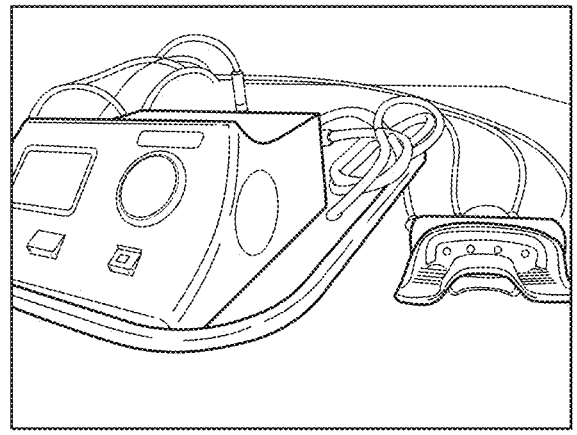
FIG. 9 shows a device for delivering electromagnetic radiation toward the tooth surface.

If the oral composition is used with electromagnetic radiation:

1) After 50 minutes of treatment with the oral composition, the electromagnetic radiation is applied toward the facial surfaces of the maxillary anterior teeth for 10 minutes;
2) The electromagnetic radiation is directed toward the maxillary anterior teeth through the oral composition;
3) The hydrophobic delivery carrier needs to allow at least about 90% of the electromagnetic radiation from 400 nm to 500 nm to pass through; and
4) The electromagnetic radiation is delivered via four fiber-optic cables (model number M71L01 from Thorlabs, Newton, N.J., USA) connected to four high power LEDs with a peak intensity wavelength of 455 nm (model number M455F1 from Thorlabs, Newton, N.J., USA) as shown in FIG. 9. The four LEDs are run at 1000 mA each using an LED Driver and Hub (model numbers DC4104 and DC4100-HUB from Thorlabs, Newton, N.J., USA). The exit ends of the four fiber-optic cables are mounted behind a transparent mouthpiece to help position the electromagnetic radiation reproducibly against the outer surface of the hydrophobic delivery carrier. The exit ends of the four fiber-optic cables are about 7 mm away from the exit surface of the mouthpiece with the electromagnetic radiation passing through the transparent mouthpiece. The bite-shelf of the mouthpiece is offset such that the transparent window through which the electromagnetic radiation passes toward the maxillary anterior teeth is 7.4 mm high. Also, the transparent window through which the electromagnetic radiation passes toward the maxillary anterior teeth is 40 mm long measured linearly from end to end (not including the curvature). The exit ends of the fiber-optic cables are positioned and angled such that the cones of electromagnetic radiation exiting from the fiber-optic cables are centered within the transparent window through which the electromagnetic radiation passes toward the maxillary anterior teeth as shown in FIG. 9. Also, the exit ends of the four fiber-optic cables are spaced such that the cones of electromagnetic radiation are spaced across the length of the transparent window through which the electromagnetic radiation passes toward the maxillary anterior teeth as shown in FIG. 9. The intensity of the electromagnetic radiation from 445 nm to 465 nm measured at the central axis of each cone of electromagnetic radiation exiting at the exit surface of the transparent window through which the electromagnetic radiation passes toward the maxillary anterior teeth needs to be from about 175 mW/cm$^2$ to about 225 mW/cm$^2$ as measured by the method disclosed herein.

Once 60 minutes of the treatment with the oral composition is completed, the polyethylene film is removed in the case of a semi-solid gel, or the article is removed in the case of a solid article. This treatment is applied once daily for a minimum of 7 days for oral compositions with less than about 1% bleaching agent, and a minimum of 3 days for oral compositions with at least about 1% bleaching agent.

The change in tooth color due to the treatment with the oral composition is measured using the procedure described below the day after the 7$^{th}$ treatment for oral compositions with less than about 1% bleaching agent and after the 3$^{rd}$ treatment for oral compositions with at least about 1% bleaching agent.

Tooth color is measured using a digital camera having a lens equipped with a polarizer filter (Camera model no. CANON EOS 70D from Canon Inc., Melville, N.Y. with NIKON 55 mm micro-NIKKOR lens with adapter). The light system is provided by Dedo lights (model number DLH2) equipped with 150 watt, 24V bulbs model number (Xenophot model number HL X64640), positioned about 30 cm apart (measured from the center of the external circular surface of one of the glass lens through which the light exits to the other) and aimed at a 45 degree angle, such that the light paths intersect at the vertical plane of the chin rest about 36 cm in front of the focal plane of the camera. Each light has a polarizing filter (Lee 201 filter), and a cutoff filter (Rosco 7 mil Thermashield filter from Rosco, Stamford, Conn., USA).

At the intersection of the light paths, a fixed chin rest is mounted for reproducible repositioning in the light field. The camera is placed between the two lights such that its focal plane is about 36 cm from the vertical plane of the chin rest. Prior to beginning the measurement of tooth color, color standards are imaged to establish calibration set-points. A Munsell N8 grey standard is imaged first. The white balance of the camera is adjusted, such that the RGB values of grey are 200. Color standards are imaged to get standard RGB values of the color chips. The color standards and grey standard are listed below (from Munsell Color, Division of X-rite, Grand Rapids, Mich., USA). Each color standard is labeled with the Munsell nomenclature. To create a grid of color standards they can be arranged in the following manner. This enables multiple color standards to be contained in a single image captured of the grid of color standards.

| Color standard grid 1 | | | | | |
|---|---|---|---|---|---|
| 7.5R 6 8 | 2.5R 6 10 | 10YR 6.5 3 | POLARIZATION CHECK | 5R 7 8 | N 3.5 0 |
| 7.5RP 6 6 | 10R 5 8 | 5YR 7 3 | 2.5Y 8.5 2 | 2.2YR 6.47 4.1 | 7.5YR 7 4 |
| 5YR 8 2 | N 8 0 | 10R 7 4 | N 8 0 | 5YR 7.5 2.5 | 2.5Y 8 4 |
| 5YR 7 3.5 | 5YR 7 2.5 | 5YR 5 2 | 5YR 7.5 2 | N 6.5 0 | N 9.5 0 |

| Color standard grid 2 | | | | | |
|---|---|---|---|---|---|
| 5YR 7.5 3.5 | 2.5Y 6 4 | 10YR 7.5 3.5 | 2.5R 7 8 | 7.5R 7 8 | 10YR 7.5 2 |
| 10YR 7.5 2.5 | N 5 0 | 2.5R 6 8 | 10YR 7 2 | 5R 7 4 | 10YR 7 2.5 |
| N 6.5 0 | 7.5RP 6 8 | 7.5R 8 4 | 5Y 8 1 | 7.5YR 8 2 | 2.2YR 6.47 4.1 |
| N 5 0 | 2.5Y 8 4 | 10YR 7 3 | N 9.5 0 | 10RP 7 4 | 2.5Y 7 2 |

| Color standard grid 3 | | | | | |
|---|---|---|---|---|---|
| 5R 6 10 | N 8.5 0 | 10YR 6.5 3.5 | 10RP 6 10 | N 8 0 | 7.5YR 7 3 |
| 2.5Y 3.5 0 | 10YR 7 3.5 | 5Y 8.5 1 | 5YR 8 2.5 | 5YR 7.5 3 | 5R 5 6 |

-continued

| Color standard grid 3 | | | | | |
|---|---|---|---|---|---|
| 10YR 7.5 3 | 5YR 6.5 3.5 | 2.5YR 5 4 | 2.5Y 8 2 | 10YR 8 2 | 2.5Y 7 2 |
| 2.5R 6 6 | 5R 7 6 | 10YR 8 2.5 | 10R 5 6 | N 6.5 0 | 7.5YR 8 3 |

For baseline tooth color, participants use a toothbrush ("Anchor 41 tuft white toothbrush" from Team Technologies, Inc. Morristown, Tenn., USA) to brush their teeth with water to remove debris from their teeth. Each participant then uses cheek retractors (from Washington Scientific Camera Company, Sumner, Wash., USA; treated with at frosted matte finish at A&B Deburring Company, Cincinnati, Ohio, USA) to pull the cheeks back and allow the facial surfaces of their teeth to be illuminated. Each participant is instructed to bite their teeth together such that the incisal edges of the maxillary incisors contact the incisal edges of the mandibular incisors. The participants are then positioned on the chin rest at the intersection of the light paths in the center of the camera view and the tooth images are captured. After all participants are imaged, the images are processed using image analysis software (Optimas manufactured by Media Cybernetics, Inc. of Silver Spring, Md.). The central four incisors are isolated and the average RGB values of the teeth are extracted.

After the participants have used a whitening product, but prior to capturing participant's tooth images, the system is set to the baseline configuration and calibrated as previously discussed. After calibration, each participant is imaged a second time using the same procedure as before making sure the participant is in the same physical position as the pre-treatment image including orientation of the teeth. The images are processed using the image analysis software to obtain the average RGB values of the central four maxillary incisors. The RGB values of all of the images are then mapped into CIE L*a*b* color space using the RGB values and the L*a*b* values of the color chips on the color standard. The L*a*b* values of the color chips on the color standard are measured using a Photo Research SpectraScan PR650 from Photo Research Inc., LA using the same lighting conditions described for capturing digital images of the facial dentition. The PR650 is positioned the same distance from the color standards as the camera. Each chip is individually measured for L*a*b* after calibration according to the manufacturer's instructions. The RGB values are then transformed into L*a*b* values using regression equations such as:

$$L^* = 25.16 + 12.02*(R/100) + 11.75*(G/100) - 2.75*(B/100) + 1.95*(G/100)^3$$

$$a^* = -2.65 + 59.22*(R/100) - 50.52*(G/100) + 0.20*(B/100) - 29.87*(R/100)^2 + 20.73*(G/100)^2 + 8.14*(R/100)^3 - 9.17(G/100)^3 + 3.64*[(B/100)^2]*[(R/100)]$$

$$b^* = -0.70 + 37.04*(R/100) + 12.65*(G/100) - 53.81*(B/100) - 18.14*(R/100)^2 + 23.16*(G/100)*(B/100) + 4.70*(R/100)^3 - 6.45*(B/100)^3$$

The $R^2$ for L*, a*, and b* should be >0.95. Each study should have its own equations.

These equations are generally valid transformations in the area of tooth color (60<L*<95, 0<a*<14, 6<b*<25). The data from each participant's set of images is then used to calculate product whitening performance in terms of changes in L*, a* and b* —a standard method used for assessing whitening benefits. When evaluating oral compositions with less than about 1% bleaching agent: Changes in L* is defined as $\Delta L^* = L^*_{day\ after\ 7\ treatments} - L^*_{baseline}$ where a positive change indicates improvement in brightness; Changes in a* (red-green balance) is defined as $\Delta a^* = a^*_{day\ after\ 7\ treatments} - a^*_{baseline}$ where a negative change indicates teeth which are less red; Changes in b* (yellow-blue balance) is defined as $\Delta b^* = b^*_{day\ after\ 7\ treatments} - b^*_{baseline}$ where a negative change indicates teeth are becoming less yellow. When evaluating oral compositions with at least about 1% bleaching agent: Changes in L* is defined as $\Delta L^* = L^*_{after\ 3\ treatments} - L^*_{baseline}$ where a positive change indicates improvement in brightness; Changes in a* (red-green balance) is defined as $\Delta a^* = a^*_{after\ 3\ treatments} - $a*baseline where a negative change indicates teeth which are less red; Changes in b* (yellow-blue balance) is defined as $\Delta b^* = b^*_{after\ 3\ treatments} - b^*_{baseline}$ where a negative change indicates teeth are becoming less yellow. $-\Delta b^*$ is used as the primary measure of bleaching efficacy. The overall color change is calculated by the equation $\Delta E = (\Delta L^{*2} + \Delta a^{*2} + \Delta b^{*2})^{1/2}$.

After using the whitening products, color changes in CIE Lab color space can be calculated for each participant based on the equations given.

Process of Making Oral Care Articles

The present invention further relates to a process of making an oral care article comprising the steps of: (i) providing a solid hydrophobic delivery carrier in the form of a strip having a length and a width forming a first surface and having a thickness extending from the first surface to a second surface, wherein the average thickness (T) may be less than about 3 mm; (ii) applying solid hydrophilic particles comprising a bleaching agent to the first surface of the solid hydrophobic delivery carrier, preferably at a level of from about 0.01% to about 15%, by total weight of the solid hydrophobic delivery carrier and solid hydrophilic particles; and (iii) forcing the solid hydrophilic particles into the first surface of the solid hydrophobic delivery carrier, thereby embedding the solid hydrophilic particles into the solid hydrophobic delivery carrier.

In one aspect, the particles are forced into the first surface of the solid hydrophobic delivery carrier under a pressure of at least about 50 pound per square inch (PSI), or at least about 500 PSI, or at least about 5000 PSI, or at least about 50,000 PSI.

In one aspect, the solid hydrophilic particles are applied only to the first surface of the solid hydrophobic delivery carrier (i.e. the solid hydrophilic particles are not applied to the second surface of the solid hydrophobic delivery carrier).

Materials present on the market, such as casting wax clear sheet 24 gauge (reference number 114009 supplied by Freeman Manufacturing Company, Ohio, USA) can be used as the solid hydrophobic delivery carrier of the present invention.

The solid hydrophilic particles may be forced or embedded in the hydrophobic delivery carrier by any suitable procedure, for example:

1. The solid hydrophilic particles may be sifted or deposited onto the hydrophobic delivery carrier and pressed in a hydraulic press for a specified period of time at a specified pressure, for example 60 seconds at 625 PSI causing the solid hydrophilic particles to become embedded in the hydrophobic delivery carrier. The material may then be cut into a suitable shape, for example a strip.
2. The solid hydrophilic particles may be sifted or deposited onto the hydrophobic delivery carrier and pressed via nip rollers at a specified pressure or gap, causing the solid hydrophobic hydrophilic particles to become embedded in the hydrophobic delivery carrier.
3. A photoreceptor drum (in combination with a corona wire and laser for example) may be used to acquire a selective surface charge that attracts the solid hydrophilic particles at the desired quantity. The photoreceptor drum may then be used to deposit the solid hydrophilic particles onto the hydrophobic delivery carrier, which may then be passed between nip rollers to embed the solid hydrophilic particles in the hydrophobic delivery carrier.
4. The surface of the hydrophobic delivery carrier may be at least partially melted (for example via a hot air stream) and immediately after the solid hydrophilic particles may be sifted or deposited onto the said partially molten surface. The hydrophobic delivery carrier may then be cooled (for example via exposure to ambient air) such that the said molten hydrophobic delivery carrier re-solidifies around at least a portion of the solid hydrophilic particles, embedding them in the hydrophobic delivery carrier.

The present invention further relates to a process for making an oral care article wherein the solid hydrophilic particles may be disposed within the hydrophobic delivery carrier by any suitable procedure, for example:

1. The material of the hydrophobic delivery carrier may also be at least partially melted or softened and the solid hydrophilic particles may be incorporated within the said partially melted or softened material by mixing or kneading. The material may then be cooled or solidified and shaped in a suitable form, for example a strip.
2. The solid hydrophilic particles may also be incorporated within the material of the hydrophobic delivery carrier by repeatedly folding the hydrophobic delivery carrier over the solid hydrophilic particles and compressing it back into a sheet in a hydraulic press. The material may then be shaped into a suitable form, for example a strip.
3. The material of the hydrophobic delivery carrier may be softened via warming until it becomes plastic, for example at about 50° C. At a plastic temperature, it can be mixed with the solid hydrophilic particles, for example in a single screw extruder, twin screw extruder, z-blade mixer, or similar equipment suitable for processing viscous materials. The mixture of plastic hydrophobic delivery carrier and solid hydrophilic particles can then be shaped into a suitable form, such as a strip or a tray, via conventional shape-forming technologies such as extrusion, injection molding, thermoforming, etc.
4. The material of the hydrophobic delivery carrier may be melted, for example at 80° C., before being mixed with the solid hydrophilic particles using conventional mixing equipment. The melted mixture can then be shaped into a suitable form, such as a strip or a tray, via conventional shape-forming technologies such as casting or injection molding.

The oral care article of the present invention can be a unit-dose article and/or a removable article. Suitable examples of an "unit-dose article" and/or an "removable article" include casting wax clear sheet 24 gauge (reference number 114009 supplied by Freeman Manufacturing Company, Ohio, USA) combined with solid hydrophilic particles comprising at least one oral care active agent, such as e.g. a bleaching agent and a) cut into a strip about 0.51 mm thick, about 22 mm wide and about 62 mm long, or b) pre-formed into a dental tray. Examples of products that are not "unit-dose article" or "removable articles" include stick type products (for example lip balm or lipstick)—because these are generally not single use products, nor are they generally removed from the oral cavity.

Referring now to the drawings, FIG. 1 shows an oral care article 10 for delivering actives agent(s) provided by solid hydrophilic particles 20 in a solid hydrophobic delivery carrier 12 as disclosed herein to the teeth and the oral cavity. The hydrophobic delivery carrier 12 is in strip form and comprises a first surface 14 having a width W from about 50 to about 80 mm and a length L from about 15 to 25 mm and second surface 16 on the opposite site of the hydrophobic delivery carrier 12. First surface 14 and second surface 16 are spaced by the bulk of the hydrophobic delivery carrier 12 having an average thickness T from about 0.15 to about 1.0 mm. The hydrophobic delivery carrier 12 in FIG. 1 is shaped in strip form which is substantially flat and may have rounded corners. A suitable strip may be a casting wax clear sheet 24 gauge (reference number 114009 supplied by Freeman Manufacturing Company, Ohio, USA) cut into a strip about 0.51 mm thick, about 22 mm wide and about 62 mm long.

The solid hydrophilic particles 20 are embedded into the hydrophobic delivery carrier 12 at the first surface 14 so that at least some of the solid hydrophilic particles 20 are in direct contact with the environment and/or may slightly protrude from the first surface 14. In contrast to the first surface 14 the second surface 16 shows less or no solid hydrophilic particles 20. The solid hydrophilic particles 20 may contain or are themselves an oral care active agent capable of influencing or effecting a desired change in appearance or structure of the surface it contacts. As discussed previously, example oral care active agents include: hydrogen peroxide, carbamide peroxide, sodium fluoride, sodium monofluorophosphate, pyrophosphate, chlorhexidine, polyphosphate, triclosan, enzymes and mixtures thereof. Examples of appearance and structural changes include, but are not necessarily limited to: stain bleaching, stain removal, remineralization to form fluorapatite, plaque removal, and tartar removal.

Figure 2:
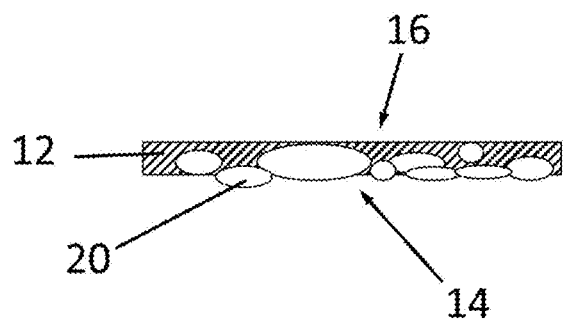
FIG. 2 is a cross-sectional view, taken along section line 2-2 of the article 10 of FIG. 1.

FIG. 2 shows a cross-sectional view, taken along section line 2-2 of the hydrophobic delivery carrier 12 shown in FIG. 1. Thereby it can be seen that the concentration of the solid hydrophilic particles 20 is greater at the first surface 14 than the concentration of the solid hydrophilic particles at the second surface 16 of the hydrophobic delivery carrier 12. In the article shown in FIG. 2 second surface 16 is nearly free of solid hydrophilic particles 20.

Figure 3:
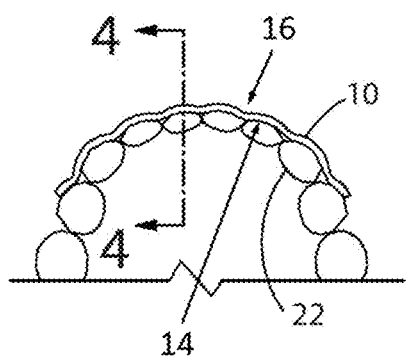
FIG. 3 is a cross-sectional plan view, showing the article 10 attached to the teeth 22.
Figure 4:
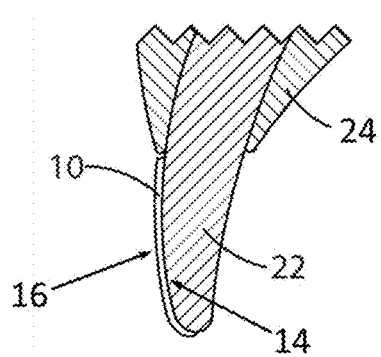
FIG. 4 is a cross-sectional elevation view of a tooth, taken along section line 4-4 of FIG. 3, showing the article 10 attached to the teeth 22.

FIGS. 3 and 4 show an article 10 of the present invention applied to the tooth surface of a plurality of adjacent teeth 22. The article 10 may be applied to the tooth surface after it has been shaped or before (FIG. 3). For example, the article 10 may be applied to the teeth with a force sufficient to shape the hydrophobic delivery carrier 12 such that it at least partially conforms to the shape of the teeth 22 such as shown in FIG. 3. Embedded in adjacent soft tissue 24 is a plurality of adjacent teeth 22 (FIG. 4). Adjacent soft tissue 24 herein defined as soft tissue surfaces surrounding the tooth structure including: papilla, marginal gingival, gingival sulcus, inter dental gingival, and gingival gum structure on lingual and buccal surfaces up to and including muco-gingival junction on the pallet. In both FIGS. 3 and 4, the article 10 is in form of a strip, wherein in one aspect, the first surface 14 comprising the higher concentration of solid hydrophilic particles 20 is arranged that it faces the teeth 22. The material of the hydrophobic delivery carrier 12 of the article 10 may have a thickness and flexural stiffness such that it can conform to the contoured surfaces of teeth 22 and to adjacent soft tissue 24. Thus, the hydrophobic delivery carrier 12 may have sufficient flexibility to form to the contours of the oral surface, the surface being a plurality of adjacent teeth 22, wherein the article 10 can be applied without significant pressure. A suitable material for the hydrophobic delivery carrier 12 of an article 10 may be a casting wax (reference number 114009 supplied by Freeman Manufacturing Company, Ohio, USA).

The hydrophobic delivery carrier 12 serves as a protective barrier for the oral care active agent provided by the solid hydrophilic particles 20 at the first surface 14. It prevents leaching or erosion of the oral care active agent via the second surface 16 for example, by the wearer's tongue, lips, and saliva. This allows the solid hydrophilic particles 20 to act upon the tooth surfaces 22 of the oral cavity for the intended period of time, for example from several minutes to several hours.

FIG. 5A is a photograph image of casting wax clear sheet 24 gauge (reference number 114009 supplied by Freeman Manufacturing Company, Ohio, USA) cut into a strip about 22 mm wide and about 62 mm long. Said strip can be directly used as hydrophobic delivery carrier 12 or the hydrophobic delivery carrier 12 is formed into a dental tray (FIGS. 5B and 5C). In one aspect, the first surface 14 of the hydrophobic delivery carrier 12 comprising the higher concentration of the solid hydrophilic particles 20 may be located at the inside of the dental tray facing the tooth surface during use, and the second surface 16 may be located at the outside of the dental tray facing the soft tissue and the tongue during use. The hydrophobic delivery carrier 12 can be formed into dental tray form with (FIG. 5C) or without (FIG. 5B) a notch 18.

Figure 6:
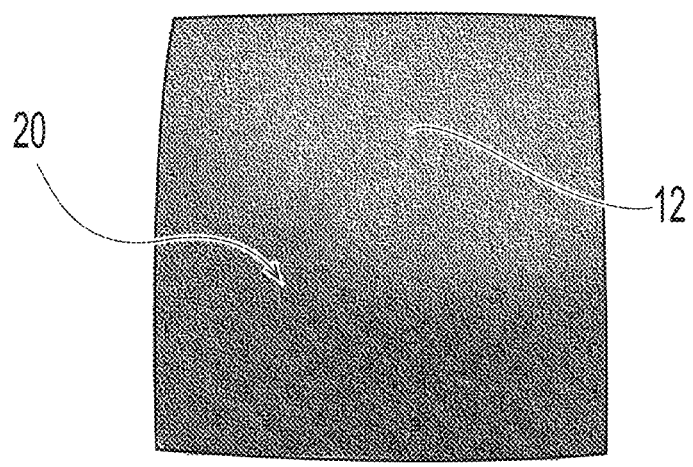
FIG. 6 is a photograph image of a sheet of wax usable as hydrophobic delivery carrier 12 comprising embedded solid hydrophilic particles 20 (Example IV-A)
Figure 7:
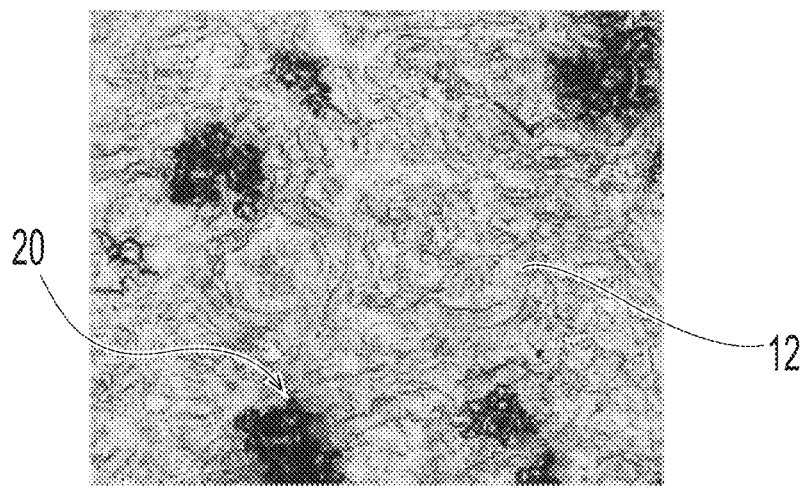
FIG. 7 is a microscope image of a sheet of wax usable as hydrophobic delivery carrier 12 comprising embedded solid hydrophilic particles 20 (Example IV-A)

FIG. 6 is a photograph image (of Example IV-A) of a sheet of casting wax (reference number 114009 supplied by Freeman Manufacturing Company, Ohio, USA) usable as hydrophobic delivery carrier 12 comprising embedded solid hydrophilic particles 20. FIG. 7 shows the same example (IV-A) in a microscope image (4× magnification).

Figure 8A:
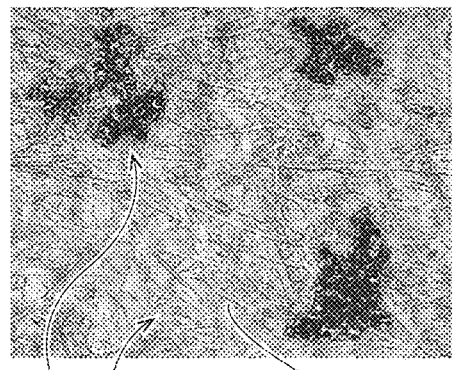
FIG. 8A and FIG. 8B are microscope images of a sheet of wax usable as hydrophobic delivery carrier 12 combined with embedded solid hydrophilic particles 20 (Example V-A)
Figure 8B:
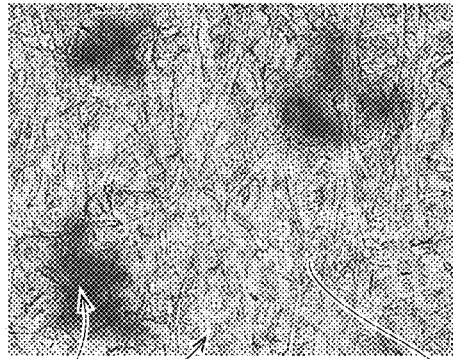

FIG. 8A and FIG. 8B are a set of microscope images (4× magnification) that show the differences between a first surface 14 Vs. a second surface 16 of Example V-A. In FIG. 8A, the solid hydrophilic particles 20 are clearly visible at a first surface—exposed directly to the external environment. In contrast in FIG. 8B, the solid hydrophilic particles 20 appear to be below the second surface 16—not exposed directly to the external environment.

Methods of Using Oral Care Articles

The present invention further relates to a method of using the oral care articles of the present invention. The oral care article can be applied to the teeth of a consumer in the dental office by a dental professional or can be used at home by the consumer. Generally, the recommended treatment period is a sufficient period of time to achieve the desired effect of the oral care active agent, for example to achieve the desired grade of bleaching.

In practicing the present invention, the user applies the article herein that contains the oral care active agent to obtain the desired effect, such as, whitening, to one or more teeth. The article can be applied with any suitable auxiliary means, or even with the fingers. The articles herein may be almost unnoticeable when applied to the teeth. After a desired period of time has elapsed, the residual article may be easily removed from the tooth surface. In general, it is not necessary to prepare the teeth before applying the present article. For example, the user may choose to brush the teeth or rinse the mouth before applying the articles of the present invention, but the surfaces of the oral cavity are neither required to be clean, nor to be dried nor to be excessively wet with saliva or water before the application.

The above-described articles and delivery systems may be combined in a kit which comprises: 1. present article and 2. instructions for use; or which comprises: 1. present article, and 2. instructions for use. If the tooth shall be radiated by electromagnetic radiation, the kit may further comprise an electromagnetic radiation source of the appropriate wavelength and instruction for use, so that the kit can be used by consumers in a convenient manner Optional Electromagnetic Radiation Treatment The article as disclosed herein, for example those comprising bleaching agents as oral care active agents may be used to whiten/bleach teeth and/or removing stain from tooth surfaces. The bleaching efficacy may be further increased by directing electromagnetic radiation of a suitable wavelength toward at least one tooth. A device suitable to provide such electromagnetic radiation is shown in FIG. 9. Electromagnetic radiation will be applied to the articles 10 as disclosed herein, if the effectiveness of the active agent provided by the solid hydrophilic particles 20 can be increased by the electromagnetic radiation. For example, electromagnetic radiation with a peak intensity wavelength of about 455 nm may increase bleaching efficacy if the active agent is a bleaching or whitening agent, such as peroxide.

A suitable wavelength may be any wavelength, which corresponds to a maximum absorption band of the tooth and/or the tooth stain to be bleached. For example, the article may be radiated with an electromagnetic radiation with one or more wavelengths in the range of from about 200 nm to about 1200 nm. The electromagnetic radiation may be directed toward at least one tooth. For example, more than one tooth may be irradiated. For example, the electromagnetic radiation may have a peak intensity at a wavelength in the range of from about 400 nm to about 500 nm, or from about 425 nm to about 475 nm, or from about 445 nm to about 465 nm, or wherein the peak intensity wavelength of the electromagnetic radiation is similar to the wavelength at which the stain absorbs the most electromagnetic radiation. Electromagnetic radiation may be directed toward at least one tooth for partial or whole wearing time of the article; or after the article has been removed from the tooth. Electromagnetic radiation may be applied at least for a sufficient period of time for whitening or a sufficient period of time to achieve the desired effect of the active, e.g. for at least about 1 minute, for at least about 5 minutes, or for at least about 10 min. The electromagnetic radiation may be applied using the procedure disclosed in US 2013/0295525. In one aspect, the article as disclosed herein is applied to at least one tooth and maintained on the at least one tooth for a first period of time; after the first period of time electromagnetic radiation is directed toward the at least one tooth for a second period of time, wherein the first period of time has a duration greater than 50%, or 80% of a total duration of the first and second periods of time; and finally, the article is removed from the at least one tooth.

Suitable sources of electromagnetic radiation include the source described herein in the section titled "Clinical Protocol".

The articles as disclosed herein may be transparent or translucent to electromagnetic radiation with wavelengths from about 400 nm to about 500 nm. For example, the articles as disclosed herein when applied in an average thickness of from about 0.05 mm to about 2 mm, or in the range of from about 0.1 mm to about 1.0 mm, or in the range from about 0.25 mm to about 0.75 mm allow from about 10%, 20%, or 30% to about 40%, 50%, 60%, 70%, 80%, 90%, or 100% of electromagnetic radiation from about 400 nm to about 500 nm to pass through, as measured by a spectrophotometer.

The electromagnetic radiation impinging on the surface of the tooth or outer surface of the hydrophobic delivery carrier, in the wavelength range from about 400 to about 500 nm may range in intensity from about 5 mW/cm2 to about 500 mW/cm2, or from about 10 mW/cm2 to about 300 mW/cm2, or from about 175 mW/cm2 to about 250 mW/cm2 measured according to the procedure specified herein.

Procedure to Measure Intensity of Electromagnetic Radiation

The intensity of the electromagnetic radiation can be measured using a spectrometer (USB 2000+ from Ocean Optics) connected to a UV-VIS 200 micron fiber-optic cable with a cosine corrector at the tip (OP 200-2-UV-VIS from Ocean Optics). The spectrometer is connected to a computer running the spectrometer software (Oceanview 1.3.4 from Ocean Optics). The tip of the fiber-optic cable is held pointing toward the light source at the location where the light intensity is to be measured. The photons collected at the detector surface are guided via the fiber-optic cable to the charge-coupled device in the spectrometer (CCD). The CCD counts photons arriving to the CCD during a pre-determined time period at each wavelength from 200 nm to 1100 nm and uses a software algorithm to convert these photon counts to spectral irradiance (mW/cm$^2$/nm). The spectral irradiance is integrated from 200 nm to 1100 nm by the software to yield the Absolute Irradiance (mW/cm$^2$), which is the intensity of electromagnetic radiation from 200 nm to 1100 nm. The spectral irradiance is integrated from 400 nm to 500 nm by the software to yield the Absolute Irradiance (mW/cm$^2$), which is the intensity of electromagnetic radiation from 400 nm to 500 nm.

For consumer convenience, the article as disclosed herein may be provided as a kit comprising the article as disclosed herein, an optional electromagnetic radiation source emitting electromagnetic radiation in a suitable wavelength, and instructions for use.

The articles of this invention are useful for both human and other animals (e.g. pets, zoo, or domestic animals) applications.

EXAMPLES

The following non-limiting examples, I-A, II-A, II-B, II-C, II-D, II-E, III-A, III-B, IV-A, V-A, VI-A, and VI-B further describe example articles within the scope of the present invention. Many variations of the example are possible without departing from the scope of the invention. All examples were performed at room temperature (RT) and atmospheric pressure unless stated otherwise.

These examples were made by 1) weighing the casting wax sheet, 2) sifting the solid hydrophilic particles (complex of hydrogen peroxide and polyvinylpyrrolidone, or urea peroxide) onto the casting wax sheet through a USA Standard Testing Sieve Number 40 with 425 micron opening, 3) sandwiching the wax sheet and particles between two sheets of paper and non-stick release liner, 4) placing the sandwich in a hydraulic press and applying a pressure of 625 psi for 60 seconds, 5) removing the wax sheet now embedded with particles and weighing it to calculate the weight of particles embedded. These sheets may be cut into shapes and sizes suitable for use in the oral cavity, for example about 22 mm wide and about 62 mm long.

|  | I-A | II-A | II-B | II-C | II-D | II-E |
|---|---|---|---|---|---|---|
| Casting wax sheet 26-gauge[1] (grams) | 3.6253 | — | — | — | — | — |
| Casting wax sheet 24-gauge[2] (grams) | — | 5.091 | 5.002 | 5.0375 | 5.0355 | 5.0359 |
| Complex of hydrogen peroxide and polyvinylpyrrolidone[3] (grams) | 0.6397 | 1.0531 | 0.9105 | 1.0567 | 1.0511 | 1.0039 |
| % H2O2 | 2.77 | 3.17 | 2.85 | 3.21 | 3.19 | 3.07 |
| % Hydrophilic particles | 15.00 | 17.14 | 15.40 | 17.34 | 17.27 | 16.57 |

[1]Casting wax sheet 26-gauge, reference number 114010, average thickness of about 0.39 mm, about 10 cm × about 10 cm square, supplied by Freeman Manufacturing Company, Ohio, USA

[2]Casting wax sheet 24-gauge, reference number 114009, average thickness of about 0.51 mm, about 10 cm × about 10 cm square, supplied by Freeman Manufacturing Company, Ohio, USA

[3]Peroxydone K-30, from Ashland Global Specialty Chemicals Inc., Covington, KY. Solubility >40 parts per 100 parts of water (estimated from information provided in Product Data Sheet from supplier on polyvinylpyrrolidone polymer K-30). Sieved through USA Standard Testing Sieve Number 40 with 425 micron opening. Contains about 17% to 20% (median 18.5%) H2O2 per information from supplier.

|  | III-A | III-B | III-C | IV-A | V-A |
|---|---|---|---|---|---|
| Casting wax sheet 26-gauge[1] (grams) | — | — | — | 3.6072 | — |
| Casting wax sheet 24-gauge[2] (grams) | 5.007 | 4.9543 | 4.9179 | — | 4.9782 |
| Complex of hydrogen peroxide and polyvinylpyrrolidone[3] (grams) | 0.0274 | 0.0286 | 0.0326 | 0.104 | 0.0168 |

-continued

|  | III-A | III-B | III-C | IV-A | V-A |
|---|---|---|---|---|---|
| % H2O2 | 0.10 | 0.11 | 0.12 | 0.52 | 0.06 |
| % Hydrophilic particles | 0.54 | 0.57 | 0.66 | 2.80 | 0.34 |

[1]Casting wax sheet 26-gauge, reference number 114010, average thickness of about 0.39 mm, about 10 cm x about 10 cm square, supplied by Freeman Manufacturing Company, Ohio, USA
[2]Casting wax sheet 24-gauge, reference number 114009, average thickness of about 0.51 mm, about 10 cm x about 10 cm square, supplied by Freeman Manufacturing Company, Ohio, USA
[3]Peroxydone K-30, from Ashland Global Specialty Chemicals Inc., Covington, KY. Solubility >40 parts per 100 parts of water (estimated from information provided in Product Data Sheet from supplier on polyvinylpyrrolidone polymer K-30). Sieved through USA Standard Testing Sieve Number 40 with 425 micron opening. Contains about 17% to 20% (median 18.5%) H2O2 per information from supplier.

|  | VI-A | VI-B |
|---|---|---|
| Casting wax sheet 24-gauge[1] (grams) | 4.9286 | 5.0906 |
| Urea Peroxide[2] (grams) | 0.4733 | 0.4848 |
| % H2O2 | 3.10 | 3.08 |
| % Hydrophilic particles | 8.76 | 8.69 |

[1]Casting wax sheet 24-gauge, reference number 114009, average thickness of about 0.51 mm, about 10 cm x about 10 cm square, supplied by Freeman Manufacturing Company, Ohio, USA
[2]Urea Hydrogen Peroxide Adduct, Catalog number L13940 from Alfa Aesar, Ward Hill, MA. Solubility in water of 800 grams per liter at 20 C. per Safety Data Sheet from supplier (80 parts per 100 parts of water). Sieved through USA Standard Testing Sieve Number 40 with 425 micron opening. Contains about 35.4% H2O2 per Wikipedia dated Sep. 22, 2020.

Comparative Example

| Comparative I-A | Crest 3D White Strips, manufactured by The Procter & Gamble Company, Cincinnati, OH, USA. Ingredients: Water, Glycerin, 9.5% H2O2, Carbomer, PVP, PEG, Acrylate copolymer, NaOH, Saccharin, and Pyrophosphate. |
|---|---|

Bleaching Efficacy

The bleaching efficacy of Example I-A (with electromagnetic radiation) Vs. Comparative Example I-A (with electromagnetic radiation) measured according to the ex-vivo procedure specified herein are listed in TABLE 1.

TABLE 1

| Bleaching Efficacy | | |
|---|---|---|
|  | Example I-A | Comparative Example I-A |
| % $H_2O_2$ | 2.77 | 9.5 |
| Description | Solid particles of PVP-peroxide embedded in wax delivery carrier | H2O2 dissolved in aqueous polymeric gel. |
| Average reduction in yellowness (−Δb* after one treatment) | 2.9 | 2.8 |

TABLE 1 shows that Example I-A delivered a similar level of reduction in yellowness (−Δb*) Vs. Comparative Example I-A (−Δb* of 2.9 Vs. 2.8) even though Example I-A had less % bleaching agent (2.77% Vs. 9.5%). These results clearly demonstrate the surprisingly similar level of efficacy of Example I-A (particles of PVP-peroxide embedded in wax delivery carrier) vs. Comparative Example I-A ($H_2O_2$ dissolved in aqueous polymeric gel), even though Example I-A had less than $⅓^{rd}$ the % bleaching agent of Comparative Example I-A. These results clearly demonstrate the surprisingly large impact of solid hydrophilic particles comprising bleaching agent as active agent embedded in wax delivery carrier on efficacy.

The bleaching efficacy of Example III-A, III-B, and III-C (samples taken from all three batches) (with electromagnetic radiation) and Comparative Example I-A (with electromagnetic radiation) measured according to the ex-vivo procedure specified herein are listed in Table 2.

TABLE 2

| Bleaching Efficacy | | |
|---|---|---|
|  | Example III-A, III-B, and III-C (samples taken from all three batches) | Comparative Example I-A |
| % $H_2O_2$ | About 0.1% | 9.5 |
| Description | Solid particles of PVP-peroxide embedded in a solid wax delivery carrier | H2O2 dissolved in aqueous polymeric gel |
| Average reduction in yellowness (−Δb*) | 2.19 (after three treatments) | 2.8 (after one treatment) |

TABLE 2 shows that Example III-A, III-B, and III-C after three treatments delivered only slightly less reduction in yellowness (−Δb*) compared to Comparative Example I-A after one treatment (2.19 Vs. 2.8) even though Example III-A, III-B and III-C had less % bleaching agent (about 0.1% Vs. 9.5%). Specifically, these results show that Example III-A, III-B, and III-C after three treatments surprisingly delivered about 78% of the reduction in yellowness of Example I-A after one treatment—this is even more surprising since Examples III-A, III-B, and III-C had only about 1% of the % bleaching agent as Comparative Example I-A. These results clearly demonstrate the surprisingly high efficacy of Example III-A, III-B, and III-C(particles of PVP-peroxide embedded in wax delivery carrier) even at very low levels of % bleaching agent—this may be especially suitable for people with sensitive teeth, or in geographies that have very stringent limits on % peroxide. These results clearly demonstrate the surprisingly large impact of solid hydrophilic particles comprising bleaching agent as active agent embedded in wax delivery carrier on efficacy.

TABLE 3

| Bleaching Efficacy | | |
|---|---|---|
|  | Example II-E | Example I-A |
| % $H_2O_2$ | 3.07 | 2.77 |
| Description | Solid particles of PVP-peroxide embedded in a solid wax delivery carrier | Solid particles of PVP-peroxide embedded in a solid wax delivery carrier |
| Average thickness of hydrophobic delivery carrier (mm) | 0.51 | 0.39 |

TABLE 3-continued

Bleaching Efficacy

|  | Example II-E | Example I-A |
|---|---|---|
| Average reduction in yellowness (−Δb* after one treatment) | 3.8 | 2.9 |

TABLE 3 shows that Example II-E delivered 31% larger reduction in yellowness (−Δb*) compared to Example I-A (3.8 Vs. 2.9) even though both articles had the same level of % bleaching agent (about 3%). Specifically, these results clearly demonstrate the surprisingly high efficacy of an article (Example II-E) made with a hydrophobic delivery carrier having an average thickness of 0.51 mm Vs. an article (Example I-A) made with a hydrophobic delivery carrier having an average thickness of only 0.39 mm, even though both compositions had the same level of $H_2O_2$ (about 3%). These results clearly demonstrate the surprisingly large impact of the average thickness of the hydrophobic delivery carrier on bleaching efficacy.

Concentration of Bleaching Agent at the Surface

The concentration of bleaching agent at the first surface Vs. second surface of Examples II-A, II-B, II-C, and II-D (samples taken from all four batches) measured according to the procedure specified herein are listed in table 4.

TABLE 4

Concentration of bleaching agent at the surface

|  | Example II-A, II-B, II-C, and II-D (samples taken from all four batches) First surface of article | Example II-A, II-B, II-C, and II-D (samples taken from all four batches) Second surface of article |
|---|---|---|
| Description | Surface of the article that is intended to contact the surface of the oral cavity to be treated (in these examples, this is also the surface of the article into which the hydrophilic particles were pressed) | Surface of the article on the far side of the first surface |
| Concentration of bleaching agent at the surface (micrograms/cm2) | 1304 | 82 |

TABLE 4 shows that the concentration of bleaching agent at the first surface is greater than the concentration of bleaching agent at the second surface (1304 micrograms/cm2 Vs. 82 micrograms/cm2). These results also show that the ratio of the concentration of bleaching agent at the first surface divided by the concentration of bleaching agent at the second surface is about 16 which is above a ratio of 1. These results clearly demonstrate the surprising ability of the present invention to deliver more active agents or bleaching agents to the surface where they are needed most.

The concentration of bleaching agent at the first surface Vs. second surface of Examples VI-A and VI-B (samples taken from both batches) measured according to the procedure specified herein are listed in table 5.

TABLE 5

Concentration of bleaching agent at the surface

|  | Example VI-A and VI-B (samples taken from both batches) First surface of article | Example VI-A and VI-B (samples taken from both batches) Second surface of article |
|---|---|---|
| Description | Surface of the article that is intended to contact the surface of the oral cavity to be treated (in these examples, this is also the surface of the article into which the hydrophilic particles were pressed) | Surface of the article on the far side of the first surface |
| Concentration of bleaching agent at the surface (micrograms/cm2) | 1457 | 43 |

TABLE 5 shows that the concentration of bleaching agent at the first surface is greater than the concentration of bleaching agent at the second surface (1457 micrograms/cm2 Vs. 43 micrograms/cm2). These results also show that the ratio of the concentration of bleaching agent at the first surface divided by the concentration of bleaching agent at the second surface is about 34 which is above a ratio of 1. These results clearly demonstrate the surprising ability of the present invention to deliver more active agents or bleaching agents to the surface where they are needed most.

The concentration of bleaching agent at the surface of Examples II-A, II-B, II-C, II-D (samples taken from all four batches), and surface of Comparative Example I-A measured according to the procedure specified herein are listed in table 6.

TABLE 6

Concentration of bleaching agent at the surface

|  | Example II-A, II-B, II-C, and II-D (samples taken from all four batches) | Comparative Example I-A Crest 3D Whitestrips |
|---|---|---|
| Description | Present invention comprising about 3% H2O2 | Comparative Example comprising about 9.5% H2O2 |
| Concentration of bleaching agent at the surface of article that is intended to contact the surface of the oral cavity to be treated (micrograms/cm2) | 1304 | 670 |

TABLE 6 shows that Examples II-A, II-B, II-C and II-D have a higher concentration of bleaching agent at the surface Vs. Comparative Example I-A (1304 micrograms/cm2 Vs. 670 micrograms/cm2), even though Examples II-A, II-B, II-C and II-D had less % bleaching agent (about 3% Vs. about 9.5%). Specifically, these results show that Examples II-A, II-B, II-C and II-D had a concentration of bleaching agent at the surface about 2× that of Comparative Example I-A, even though Examples II-A, II-B, II-C and II-D had less than $1/3^{rd}$ the % bleaching agent of Comparative Example I-A. These results clearly demonstrate the surprising ability of the present invention to deliver more active agents or bleaching agents to the surface where they are needed most.

Number of Solid Particles at a Surface

The number of solid particles at a first surface and second surface of Example V-A counted according to the procedure specified herein are listed in table 7.

TABLE 7

Number of particles at a surface

| | Example V-A First surface of article | Example V-A Second surface of article |
|---|---|---|
| Description | Surface of the article that is intended to contact the surface of the oral cavity to be treated (in this example, this is also the surface of the article into which the hydrophilic particles were pressed) | Surface of the article on the far side of the first surface |
| Average number of solid particles per cm2 at the surface | 24.6 | 1 |

Table 7 shows that the number of solid particles per cm2 at the first surface of Example V-A is greater than the number at the second surface (24.6 Vs. 1 per cm2). These data show that the ratio of the number of particles per cm2 at the first surface divided by the number of particles per cm2 at the second surface of Example V-A is about 24.6, which is above a ratio of 1.

Ex-Vivo Procedure to Measure Bleaching Efficacy

1. Cut a circular disc (7.2 mm to 7.8 mm diameter×1.2 mm to 1.3 mm thickness) out of the front surface of a human incisor tooth. Leave the facial surface intact and flatten the lingual surface that has been cut out of the tooth. Store the tooth-disc in 15 to 20 ml of water that meets USP specification in a glass vial for at least eighteen hours. Repeat this for a total of 12 teeth.

2. Measure the baseline L* and b* of the facial surface of each tooth-disc individually placed on a standard white background (White reference card used for digital & film photography, for example DGK-XL X000B1R417 from DGK Color Tools) using a hand-held spectrophotometer Konica Minolta 700d. The Konica Minolta 700d spectrophotometer is used with an aperture of about 6.3 mm diameter, the observer angle is set at 2 degrees, the illuminant is set at daylight color temperature of 5003K, and specular reflection is excluded. To control the moisture level in the tooth-disc during these measurements, a circular disc of about 19 mm diameter is cut from a clear flexible polyethylene film from about 0.01 mm to about 0.02 mm thick and placed over the tooth-disc as soon as it is taken out of the water and the L* and b* values are measured through this polyethylene-disc. Take a set of three measurements per day on three separate days. Store the tooth-disc in 15 to 20 ml of water that meets USP specification in a glass vial for at least eighteen hours after each set of three measurements. Calculate the average baseline L* and b* for each tooth-disc across all three days.

3. Treat each tooth-disc individually with the composition to be assessed. If the composition is a solid article, a) take the tooth-disc out of the water and place the article on the facial surface of the tooth-disc while it is still wet, and b) briefly apply pressure to the article to simulate the article being positioned on the teeth. If the composition is a semisolid gel, a) take the tooth-disc out of the water and sandwich about 0.04 gram to about 0.05 gram of the gel between the tooth-disc and a polyethylene-disc (about 19 mm in diameter cut from a clear flexible polyethylene film from about 0.01 mm to about 0.02 mm thick), and b) briefly apply pressure to the polyethylene-disc to simulate the gel being applied to the teeth. Place this sandwich of tooth-disc+article or tooth-disc+gel+polyethylene-disc in an oven at about 34C (to simulate the conditions of the facial surface of maxillary anterior teeth) for about 60 minutes.

4. If the composition is used with electromagnetic radiation:

After 50 minutes of treatment with the composition, the electromagnetic radiation is applied toward the facial surface of the tooth-disc for 10 minutes.

The electromagnetic radiation is directed toward the facial surface of the tooth-disc through the article or through the gel+polyethylene-disc.

The electromagnetic radiation is delivered via a fiber-optic cable (model number M71L01 from Thorlabs, Newton, N.J., USA) connected to a high power LED with a peak intensity wavelength of 455 nm (model number M455F1 from Thorlabs, Newton, N.J., USA). The LED is run at 1000 mA using an LED Driver (model number DC2100, or DC4104 paired with DC4100-HUB from Thorlabs, Newton, N.J., USA). The exit end of the fiber-optic cable is mounted to help position the electromagnetic radiation reproducibly against the outer surface of the strip. The exit end of the fiber-optic cable is about 7 mm away from the tooth surface. The intensity of the electromagnetic radiation from 400 nm to 500 nm measured at the central axis of the cone of electromagnetic radiation at this distance needs to be from about 175 mW/cm$^2$ to about 225 mW/cm$^2$ as measured by the method disclosed herein.

This radiation is applied for about 10 minutes per tooth-disc.

5. Once 60 minutes of the treatment with the composition is completed, the residual composition is removed from the tooth-disc using a paper-towel and water.

6. After each treatment, store the tooth-disc in 15 to 20 ml of water that meets USP specification in a glass vial for at least eighteen hours. 7. Eighteen (or more) hours after the final treatment, measure the post-treatment b* of each tooth-disc individually using the procedure specified previously for the tooth-discs. This is done on three subsequent days and averaged across all three days for each tooth-disc.

8. For each tooth-disc, calculate the change in b* (yellow-blue balance) as $\Delta b^* = b^*_{post-treatment} - b^*_{baseline}$ where a negative change indicates the tooth-disc has become less yellow. $-\Delta b^*$ is used as the primary measure of bleaching efficacy. Calculate the average reduction in yellowness ($-\Delta b^*$) across all tooth-discs.

Procedure to Measure the Concentration of Active Agent at A Surface of a Hydrophobic Delivery Carrier Comprising Active Agent (i.e. The Article)

The concentration of active agent at the surface of a hydrophobic delivery carrier comprising active agent (i.e. the article) is measured according to the following procedure.

1. Cut a disc about 19 mm in diameter out of the article and record its weight.

2. Weigh 0.425 g+/−0.003 g of water to a small plastic weigh boat.

3. With a pair of tweezers place the disc on the water with the surface to be tested in contact with the water. Make sure the water reaches the perimeter of the disc but does not flow over on top of the disc.
4. After 2 minutes, remove the disc and hold it vertically to drip back into the weigh boat for 5 seconds.
5. Assay the water for % active agent.
6. Calculate the total micrograms of active agent in the water based on the original amount of water added (0.425 g); and divide this by the surface area of the disc contacted with the water in cm2. This value (in micrograms/cm2) is the concentration of active agent at the surface of the disc tested.
7. Perform steps 1 to 6 on a total of 24 discs and average all 24 values. This average value (in micrograms/cm2) is the concentration of active agent of the article at the surface tested.

To validate the above procedure, the concentration of hydrogen peroxide at the first surface (gel-surface) of Comparative Example I-A must be measured and demonstrated to be from 550 micrograms/cm2 to 800 micrograms/cm2.

Procedure to Count the Number of Particles at a Surface of A Hydrophobic Delivery Carrier Comprising Active Agent (i.e. The Article)

The number of particles at a surface of a hydrophobic delivery carrier comprising active agent (i.e. the article) is measured according to the following procedure.

1. Cut 24 squares of 1 cm×1 cm each from the article
2. Count the number of particles at the surface using a microscope in each square.
3. Average the number particles counted at the surface across all 24 squares. This is the number of particles/cm2 at that surface.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oral care article comprising:
a) a solid hydrophobic delivery carrier in the form of a strip having a length and a width forming a first surface and having a thickness extending from the first surface to a second surface, wherein an average thickness is less than about 3 mm; and
b) solid hydrophilic particles comprising an active agent for oral care comprising at least one of healing agent(s), anti-calculus agent(s), anti-caries agent(s), antimicrobial agent(s), dentinal desensitizing agent(s), anesthetic agent(s), antifungal agent(s), coolant(s), anti-inflammatory agent(s), selective H-2 antagonist(s), nutrient(s), erythritol, probiotics, fluoride ion source(s), hydrophilic bleaching agent(s), tooth whitening agent(s), or combinations thereof;
wherein the solid hydrophilic particles are disposed in and embedded in the solid hydrophobic delivery carrier, wherein the solid hydrophilic particles are disposed i) at least partially below the first surface, and ii) at least partially at or above the first surface of the solid hydrophobic delivery carrier; and
wherein a concentration of the active agent at the first surface is greater than a concentration of the active agent at the second surface.

2. The oral care article according to claim 1, wherein the concentration of active agent at the first surface is from about 10 micrograms/cm$^2$ to about 5000 micrograms/cm$^2$.

3. The oral care article according to claim 1, wherein a number of the solid hydrophilic particles per cm$^2$ at the first surface is from about 10 to about 1000.

4. The oral care article according to claim 1, wherein the concentration of active agent at the second surface is from about 0.001 micrograms/cm$^2$ to about 500 micrograms/cm$^2$.

5. The oral care article according to claim 1, wherein a number of solid hydrophilic particles per cm$^2$ at the second surface is no greater than about 200.

6. The oral care article according to claim 1, wherein a ratio of the concentration of active agent at the first surface to the concentration of active agent at the second surface is greater than 1.

7. The oral care article according to claim 1, wherein a number-average equivalent-diameter or a volume-average equivalent-diameter of the solid hydrophilic particles is from about 0.01 microns to about 2000 microns.

8. The oral care article according to claim 1, wherein the average thickness of the hydrophobic delivery carrier and/or article is less than about 3 mm.

9. The oral care article according to claim 1, wherein a ratio of an average thickness of the hydrophobic delivery carrier and/or the article divided by a number-average equivalent-diameter or a volume-average equivalent-diameter of the solid hydrophilic particles is from about 0.01 to about 100.

10. The oral care article according to claim 1, wherein the article and/or hydrophobic delivery carrier is a single layer and/or is shaped in a form of a dental arch.

11. The oral care article according to claim 1, wherein an overall concentration of active agent is from about 0.001% to about 15%, by weight of the article.

12. The oral care article according to claim 1, wherein an overall concentration of active agent is from about 0.01% to about 5%, by weight of the article.

13. The oral care article according to claim 1, wherein the active agent comprises a bleaching agent, and the article comprises less than about 10%, by weight of the article, of the bleaching agent.

14. The oral care article according to claim 1, wherein the hydrophobic delivery carrier comprises a material having: (i) a needle penetration consistency value of from about 0.1 to about 100 as measured by ASTM D1321-16a; and/or (ii)

a cone penetration consistency value of less than about 10 as measured by ASTM D937-07; and/or (iii) a drop melting point of from about 60° C. to about 120° C. as measured by ASTM D127-08.

15. The oral care article according to claim 1, wherein the hydrophobic delivery carrier comprises a material having: (i) a needle penetration consistency value of from about 1 to about 10 as measured by ASTM D1321-16a; and/or (ii) a cone penetration consistency value of less than about 5 as measured by ASTM D937-07; and/or (iii) a drop melting point of from about 80° C. to about 100° C. as measured by ASTM D127-08.

16. The oral care article according to any claim 1, wherein the hydrophobic delivery carrier comprises a wax, a polymer, or a combination thereof.

17. The oral care article according to claim 1, wherein the hydrophobic delivery carrier comprises microcrystalline wax and/or polyethylene polymer.

18. The oral care article according to claim 1, wherein the article is a unit-dose article and/or a removable article.

19. The oral care article according to claim 1, wherein more than about 50% of a volume of the solid hydrophilic particles is disposed below or at the first surface of the hydrophobic delivery carrier.

20. The oral care article according to claim 1, wherein more than about 10% of a surface area of the solid hydrophilic particles is disposed at the first surface of the hydrophobic delivery carrier and exposed to an external environment surrounding the hydrophobic delivery carrier.

21. The oral care article according to claim 1, wherein the active agent comprises: (i) a complex of hydrogen peroxide and polyvinylpyrrolidone (PVP) polymer, (ii) urea peroxide, or (iii) mixtures thereof.

22. A method for delivering health benefits to the oral cavity comprising reducing and/or removing caries, plaque, tartar and stain, promoting gum health, preventing and treating cavities, improving breath, promoting bleaching, providing antibacterial effects, or a combination thereof, by applying the oral care article of claim 1 to the oral cavity.

23. A kit comprising the oral care article according to claim 1 and an electromagnetic radiation source capable of directing electromagnetic radiation with one or more wavelengths in the range from about 200 nm to about 1700 nm towards at least one tooth impinging on the outer surface of the hydrophobic delivery carrier in the range from about 175 mW/cm$^2$ to about 225 mW/cm$^2$.

24. A process for making an oral care article, the process comprising the steps of:
 (i) providing a solid hydrophobic delivery carrier in the form of a strip having a length and a width forming a first surface and having a thickness extending from the first surface to a second surface, wherein an average thickness is less than about 3 mm;
 (ii) applying solid hydrophilic particles comprising a bleaching agent to the first surface of the solid hydrophobic delivery carrier, at a level of from about 0.01% to about 15%, by total weight of the oral care article; and
 (iii) forcing the solid hydrophilic particles into the first surface of the solid hydrophobic delivery carrier, thereby embedding the solid hydrophilic particles into the solid hydrophobic delivery carrier.

25. The process according to claim 24, wherein the solid hydrophilic particles are applied only to the first surface of the solid hydrophobic delivery carrier.

26. The process according to claim 24, wherein the solid hydrophilic particles are forced into the first surface of the solid hydrophobic delivery carrier under a pressure of at least about 50 pounds per square inch (PSI).

* * * * *